United States Patent [19]

Kock

[11] 3,940,169

[45] Feb. 24, 1976

[54] LOOP KNOT TYING METHOD AND APPARATUS

[75] Inventor: Ronald W. Kock, Cincinnati, Ohio

[73] Assignee: The Procter & Gamble Company, Cincinnati, Ohio

[22] Filed: Oct. 22, 1974

[21] Appl. No.: 517,110

[52] U.S. Cl.................................. 289/1.5; 289/18
[51] Int. Cl.²........................................ B65H 69/04
[58] Field of Search .......... 289/1.5, 2, 18; 19/144.5

[56] References Cited
UNITED STATES PATENTS

| | | | |
|---|---|---|---|
| 3,092,952 | 6/1963 | Johansson | 289/2 X |
| 3,348,866 | 10/1967 | Etz | 289/18 |
| 3,814,469 | 6/1974 | Simon | 289/1.5 |

Primary Examiner—Louis K. Rimrodt
Attorney, Agent, or Firm—Melville, Strasser, Foster & Hoffman

[57] ABSTRACT

A process and apparatus for forming from string a simple loop knot either through or about a product. While individual products may be hand-fed to the apparatus, the apparatus is adapted to perform the process continuously, rapidly and automatically upon a product in the form of a continuous flexible web utilizing a single, continuous, external string source. In an exemplary embodiment the apparatus comprises a rotating drum carrying a plurality of identical heads, each head operating upon a segment of the product web to form individual loop knotted products therefrom. Although the number of operations performed by each head upon the product web may be varied, in the exemplary embodiment to be described each head is provided with operating instrumentalities to pleat the web, clamp the pleated web, seal the web at a glue stripe printed thereon, meter the correct length of string, cut the metered string, pierce the pleated web, form a simple loop knot through the pierced hole and about the side of the web, cut the web and display a finished individual product by its string for pick-up by a discharge transfer means.

44 Claims, 43 Drawing Figures

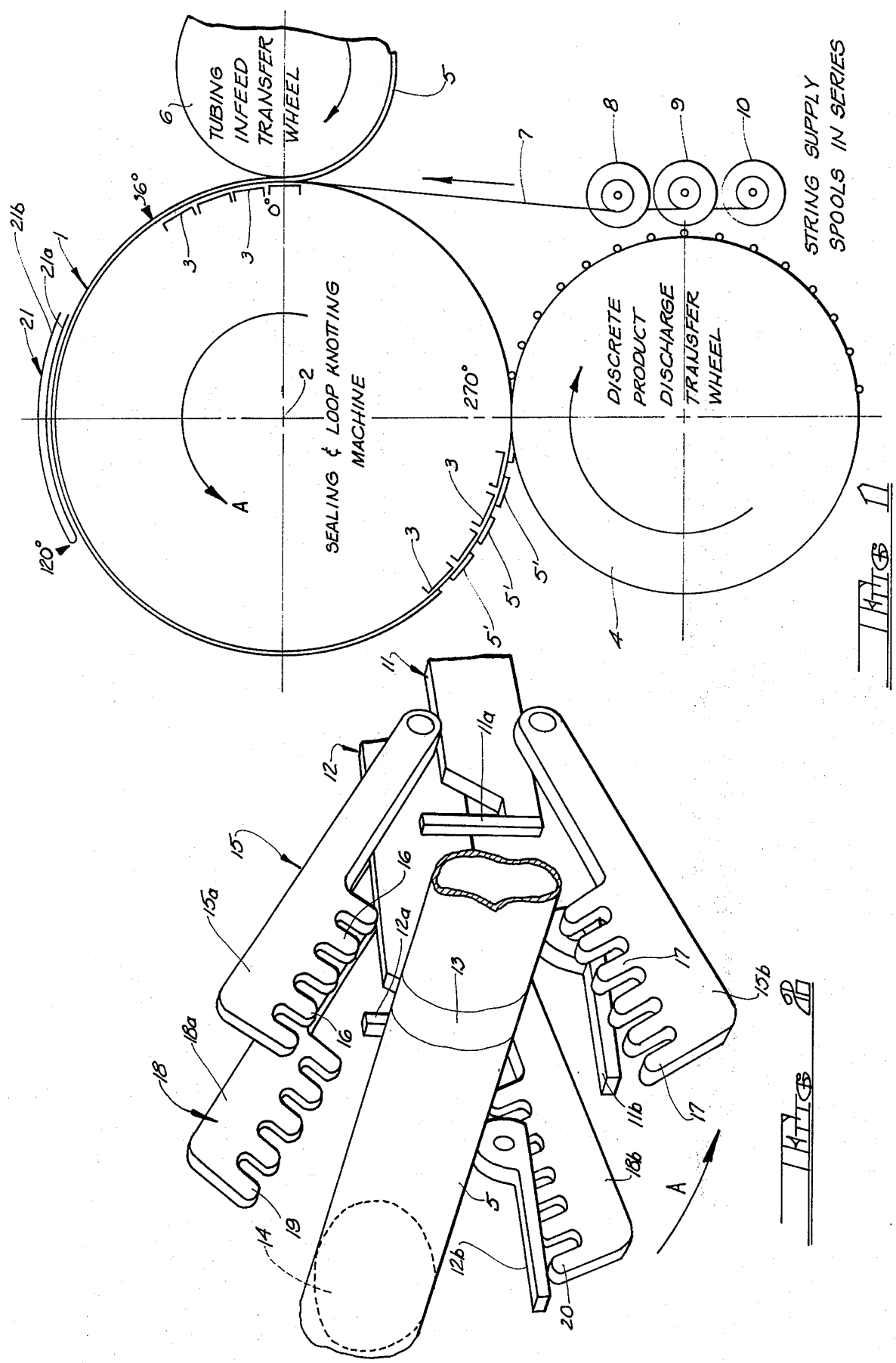

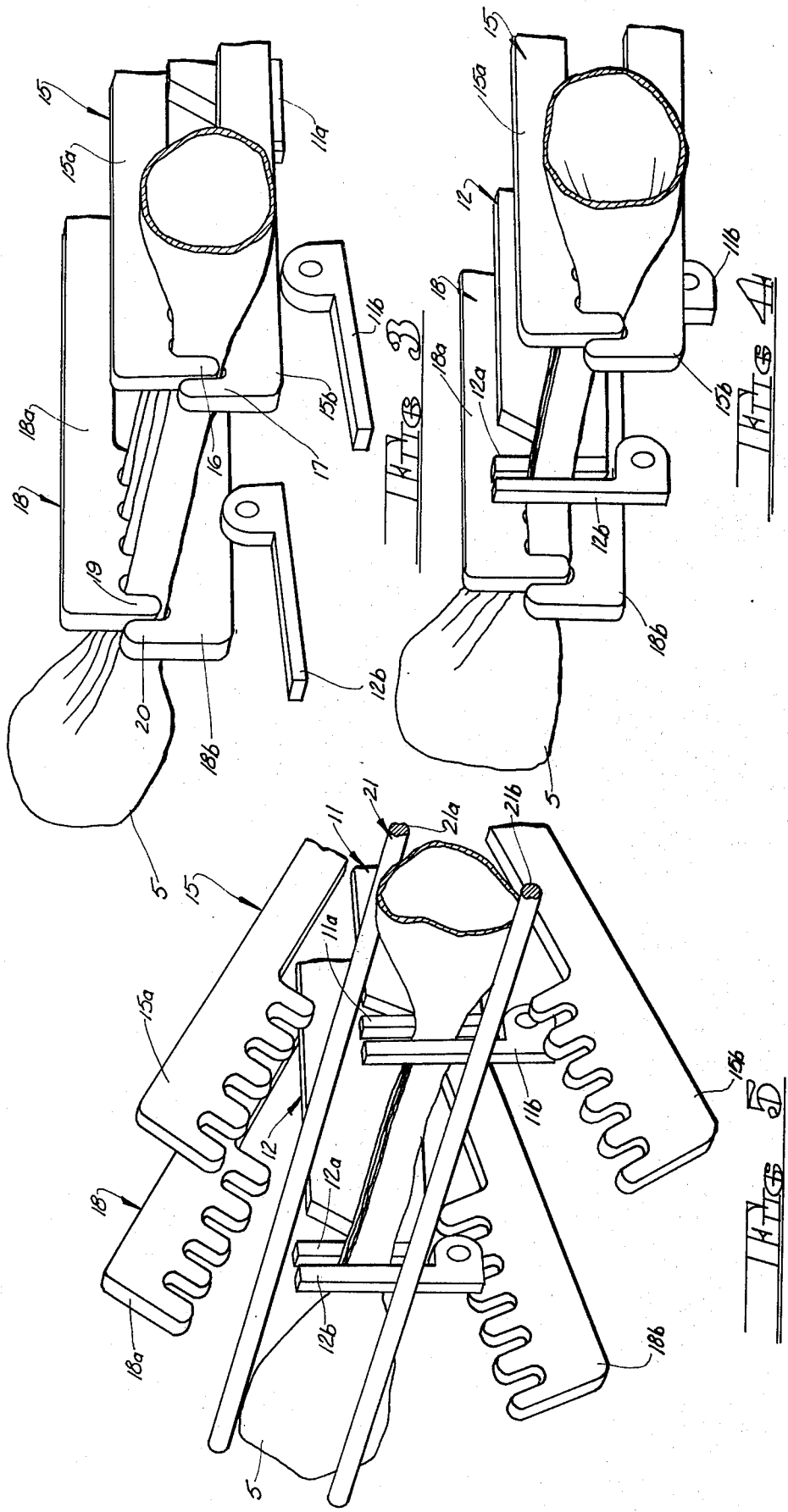

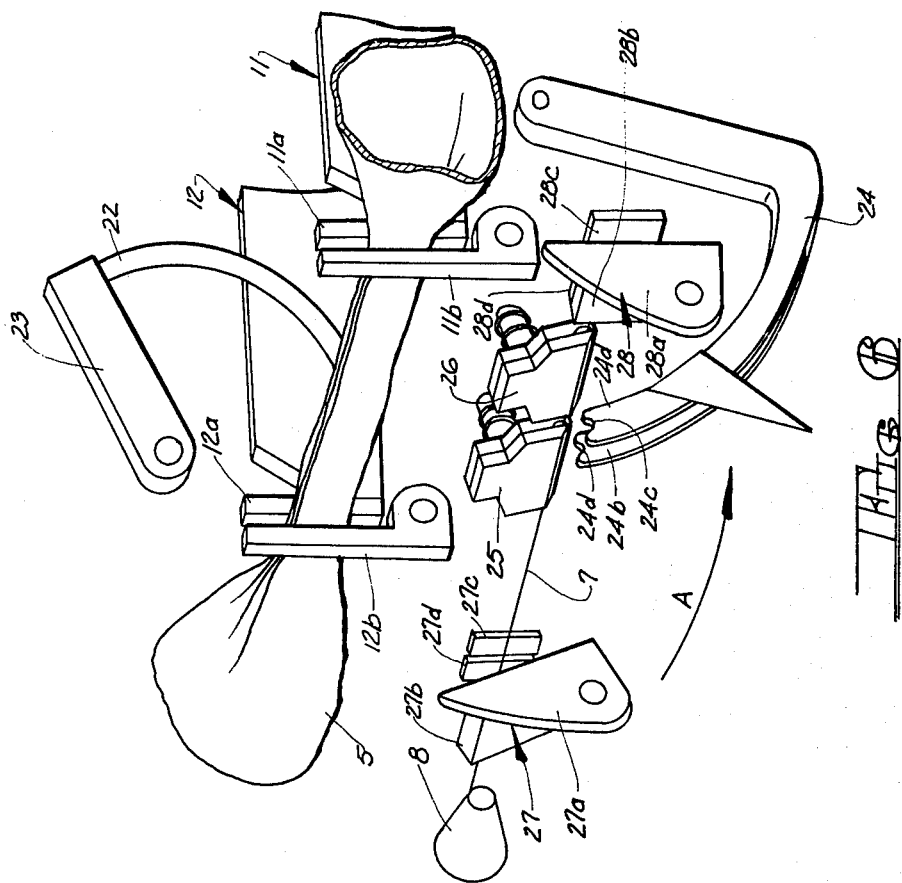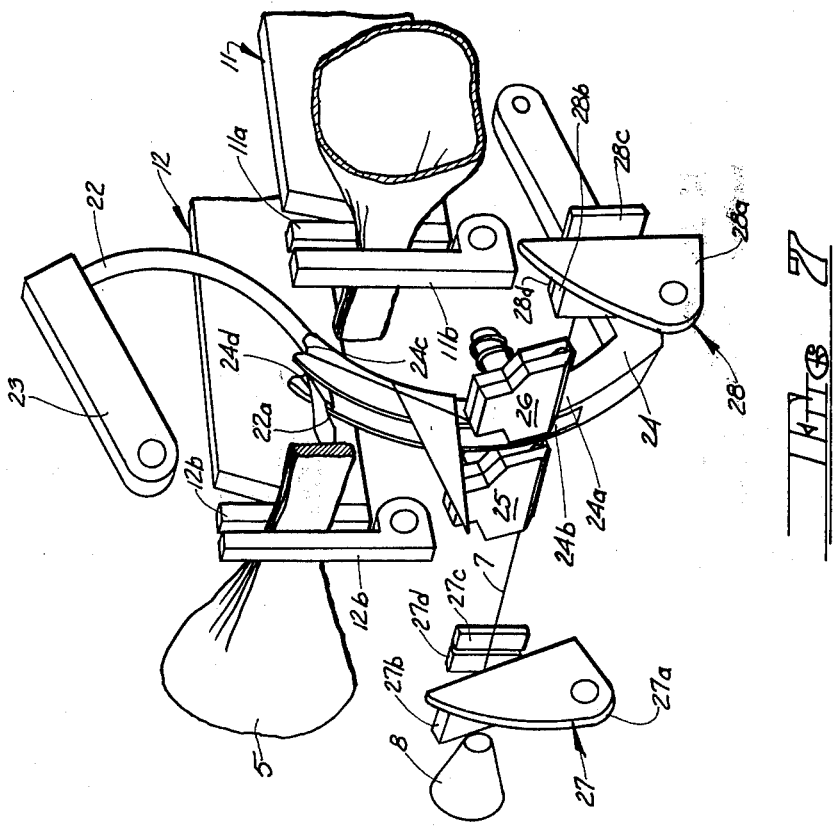

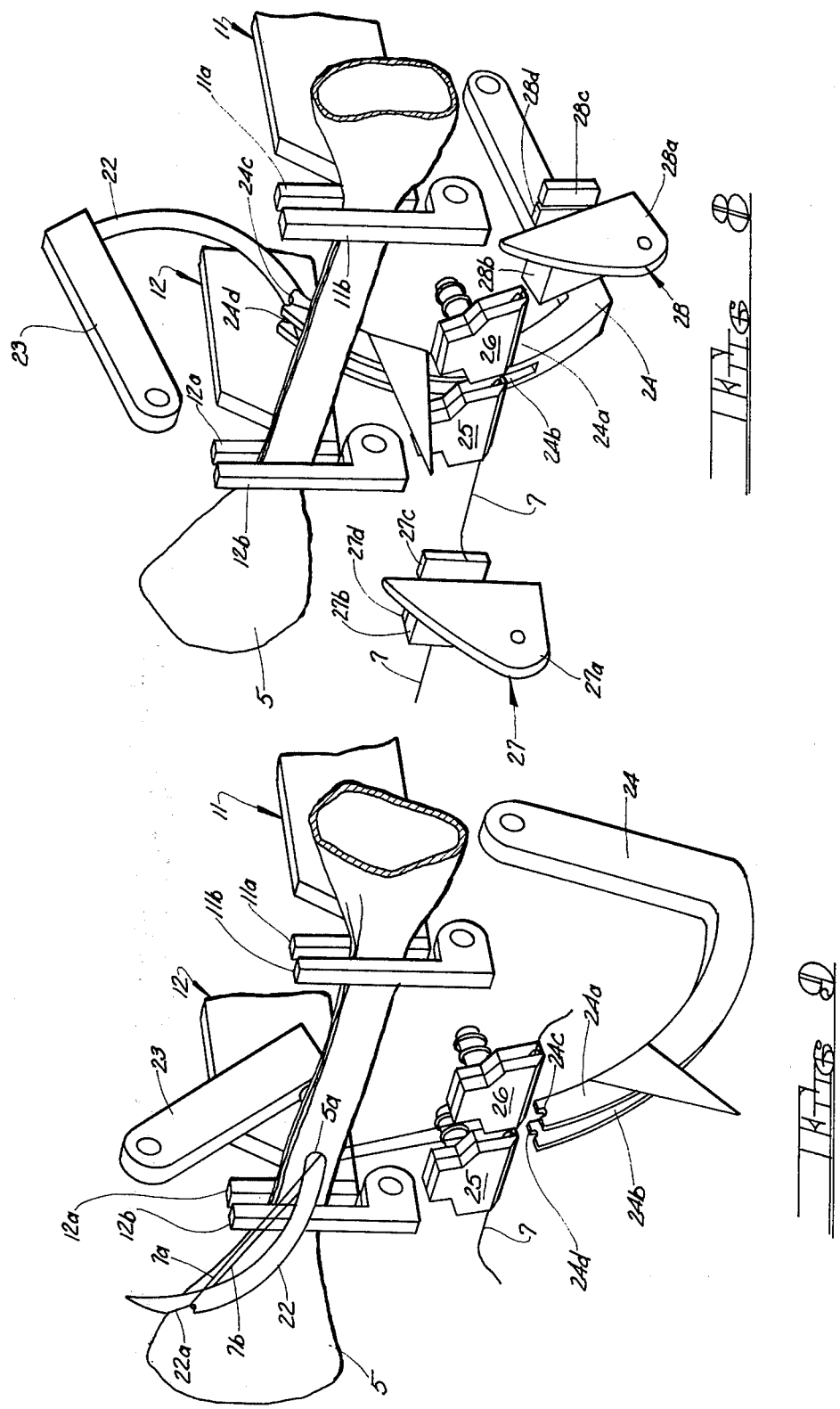

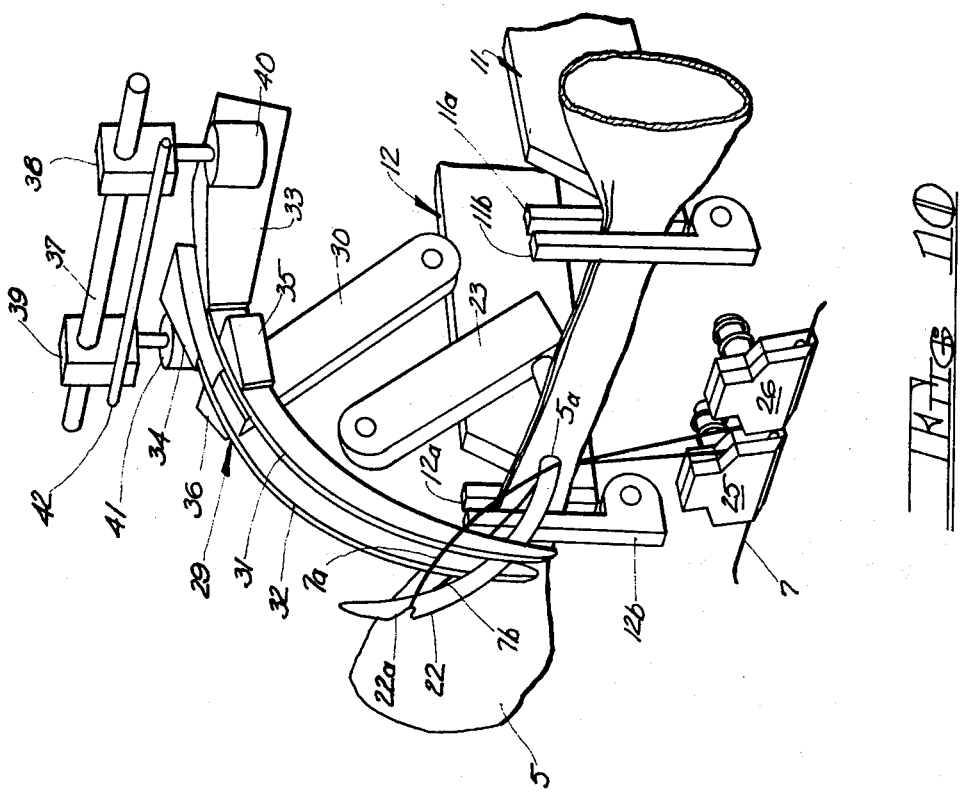
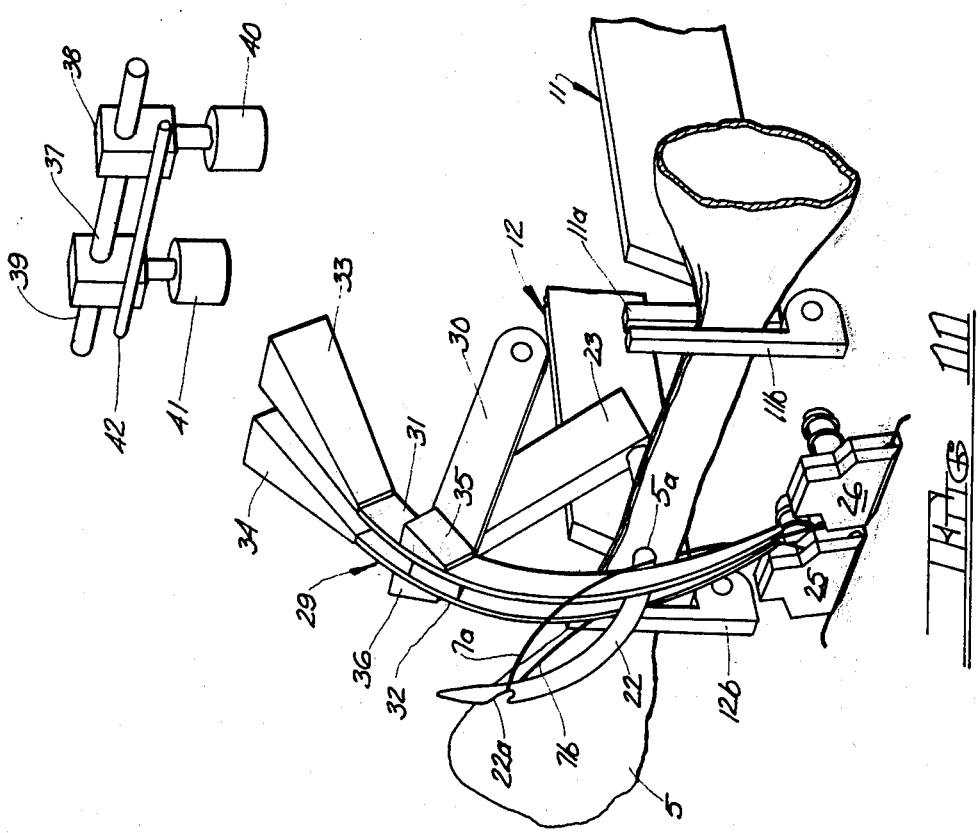

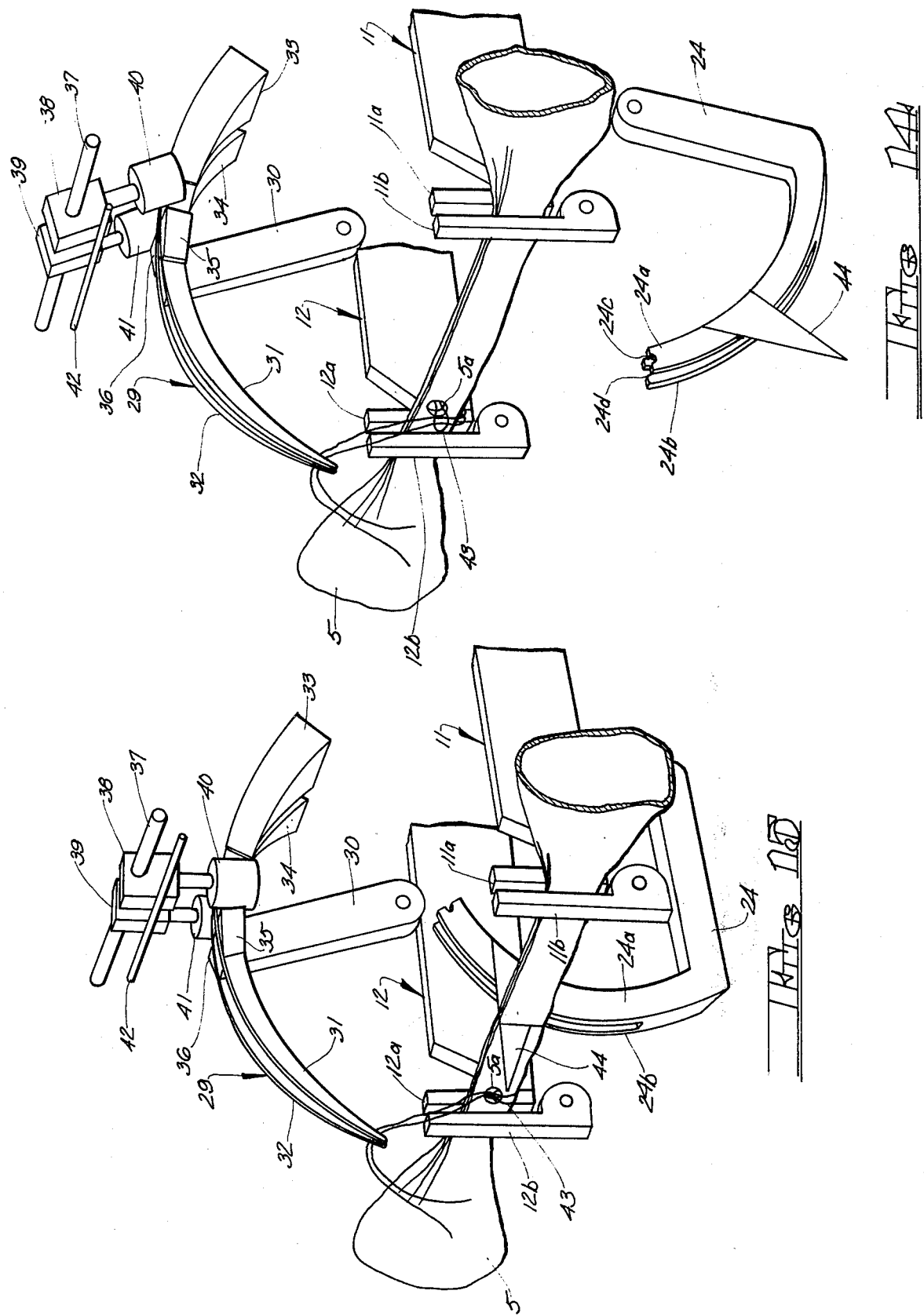

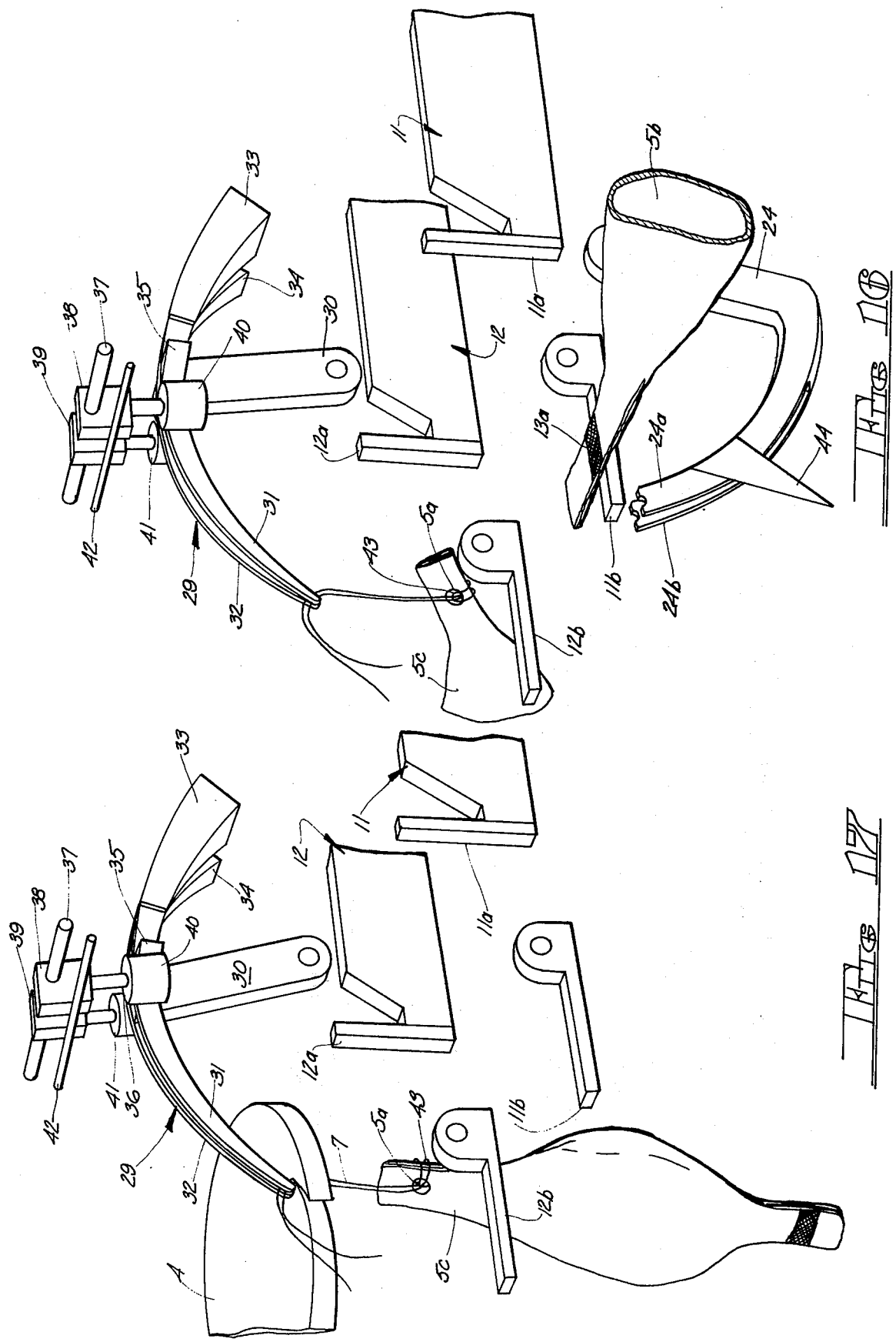

FIG. 18

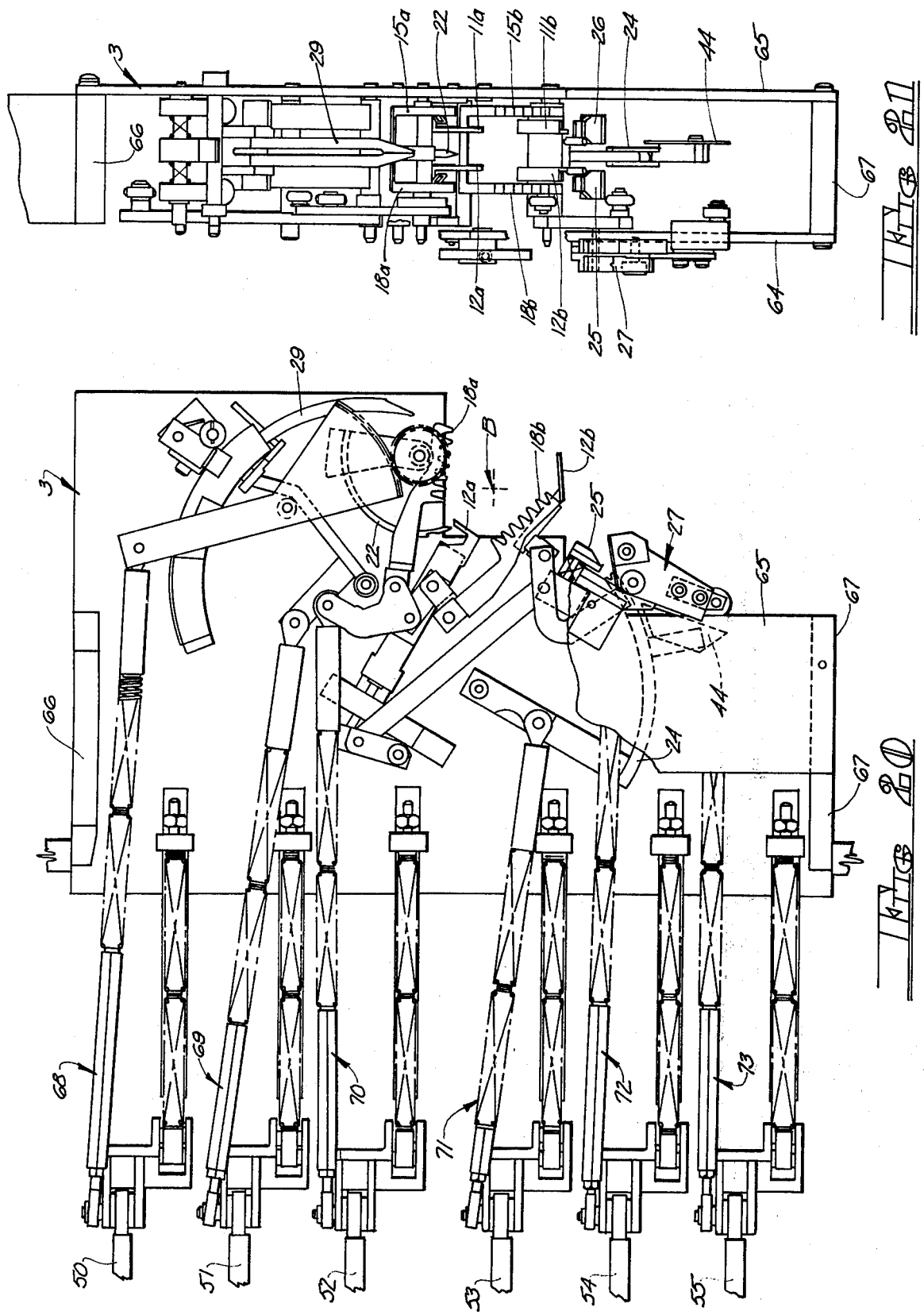

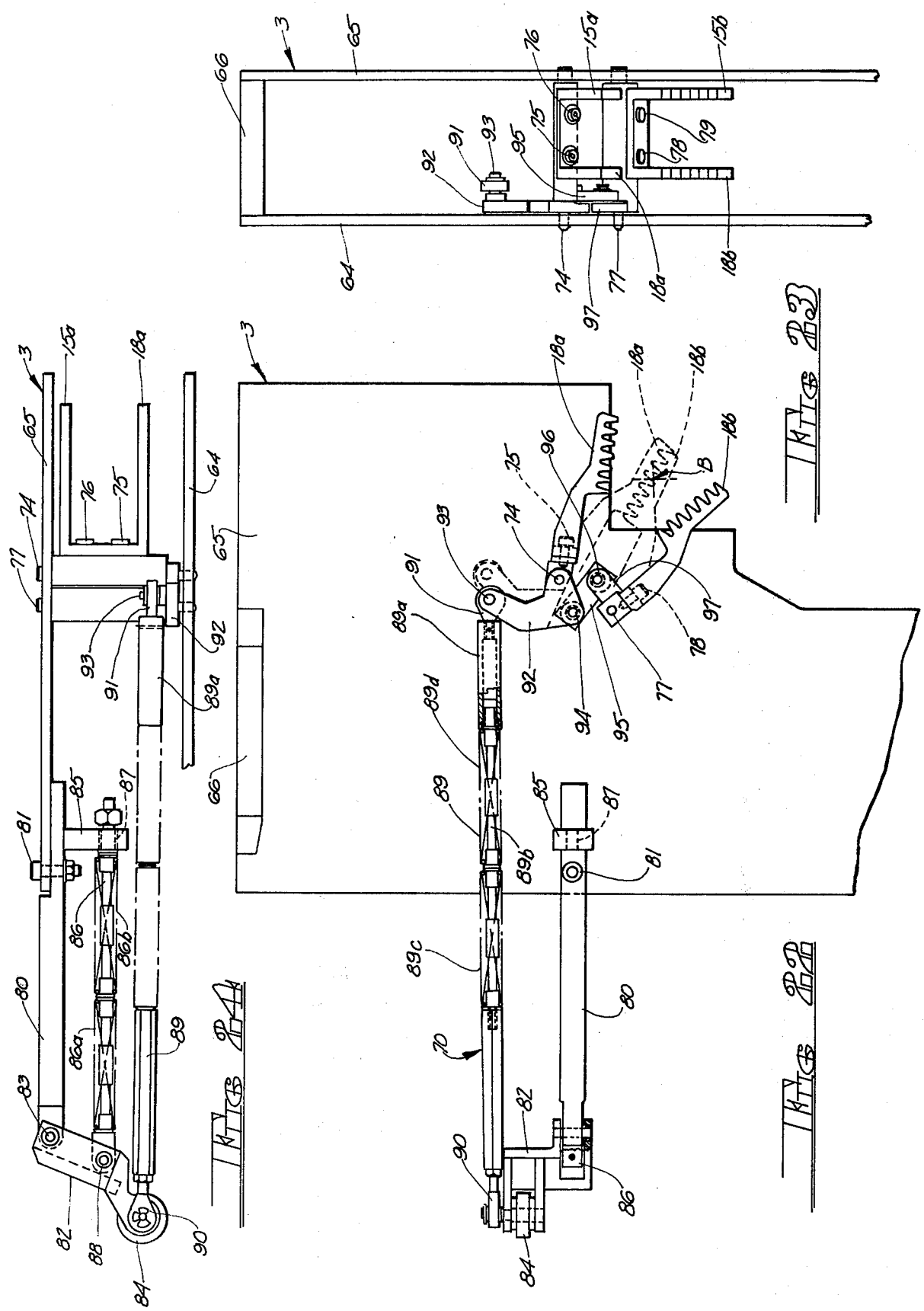

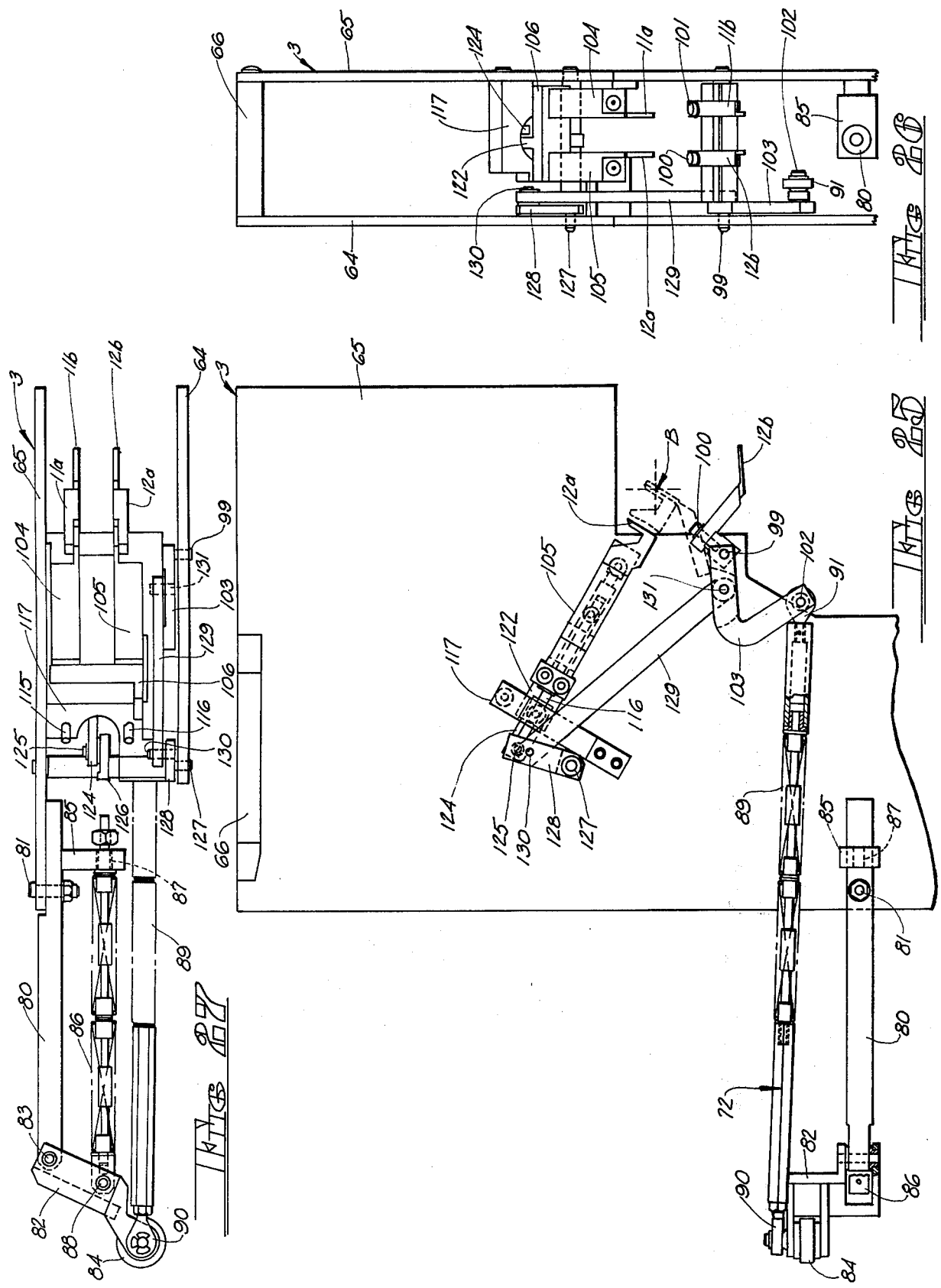

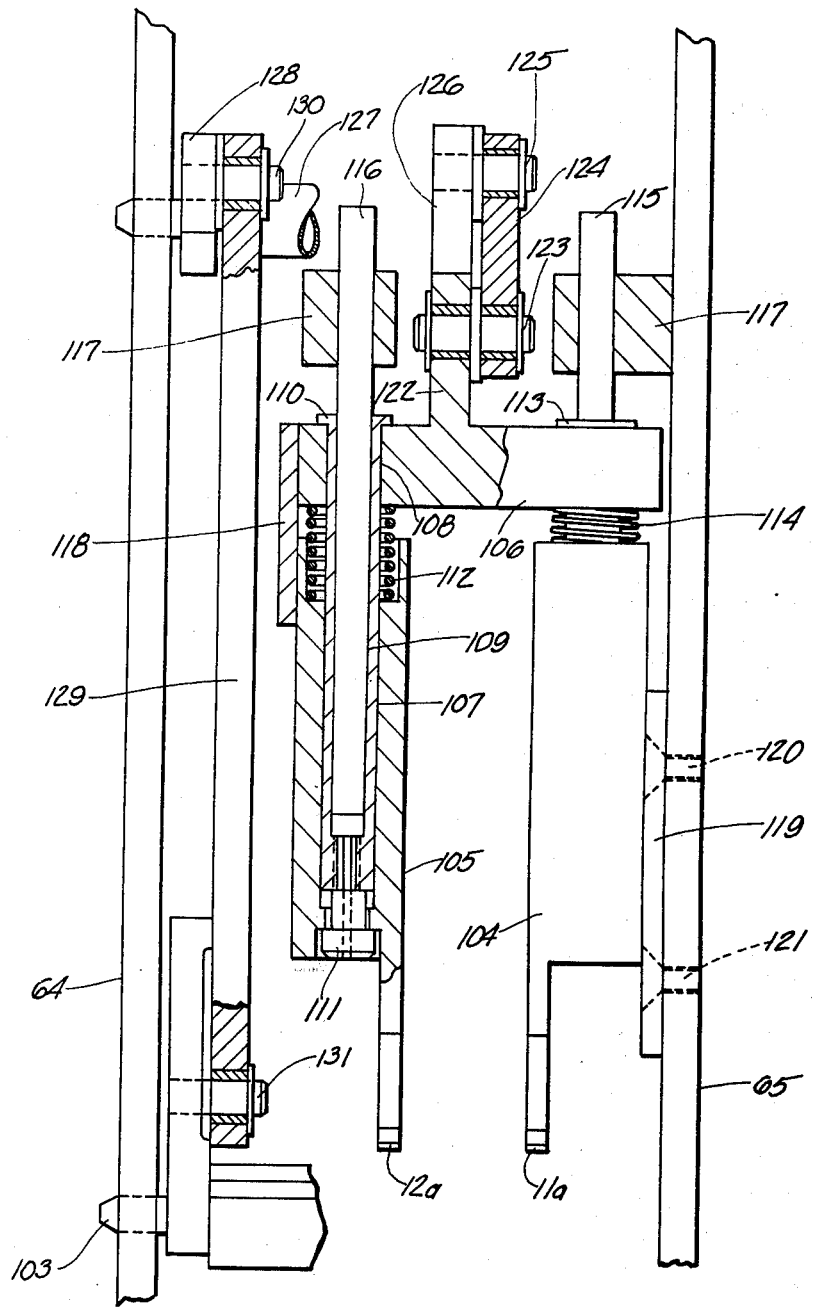

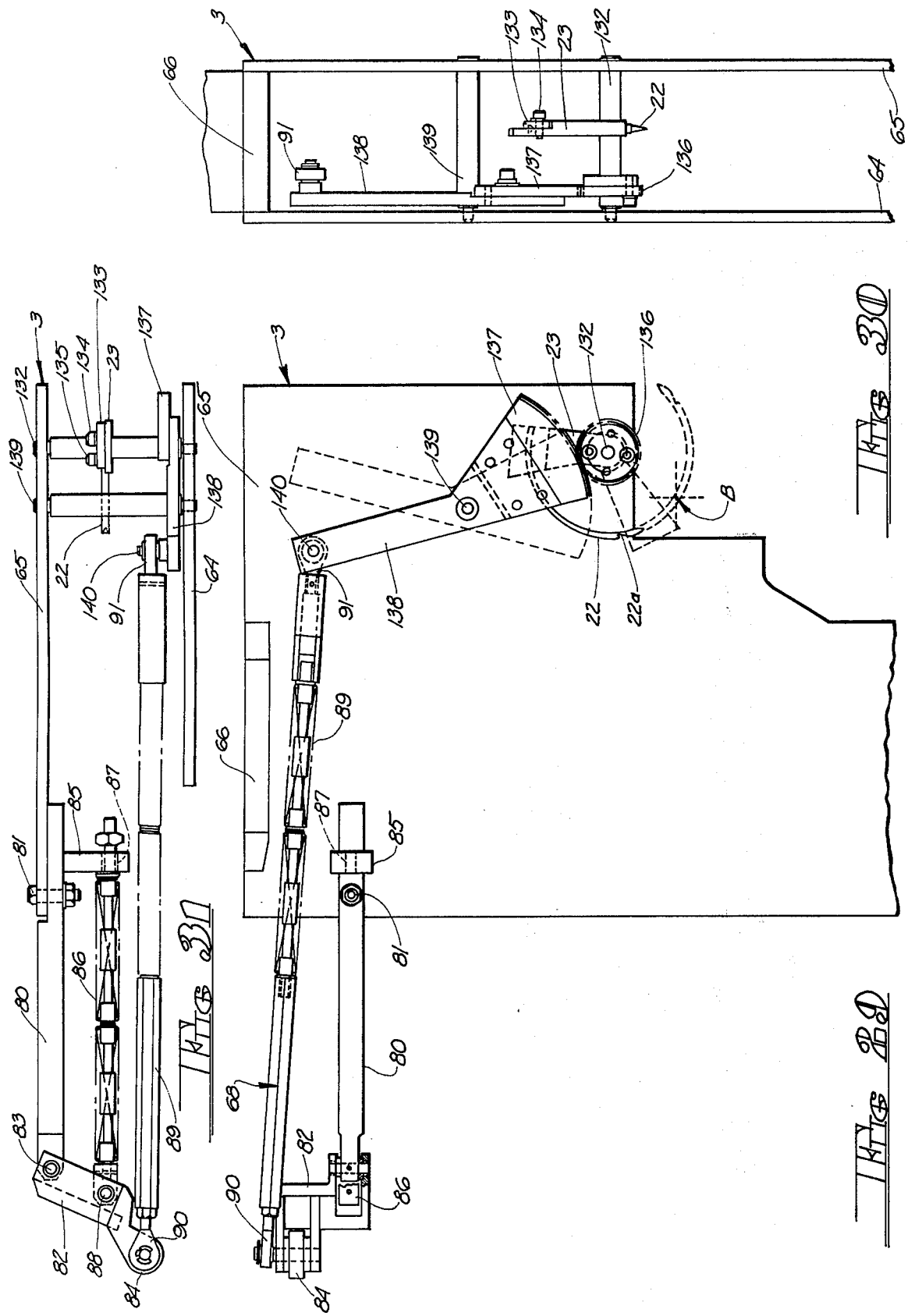

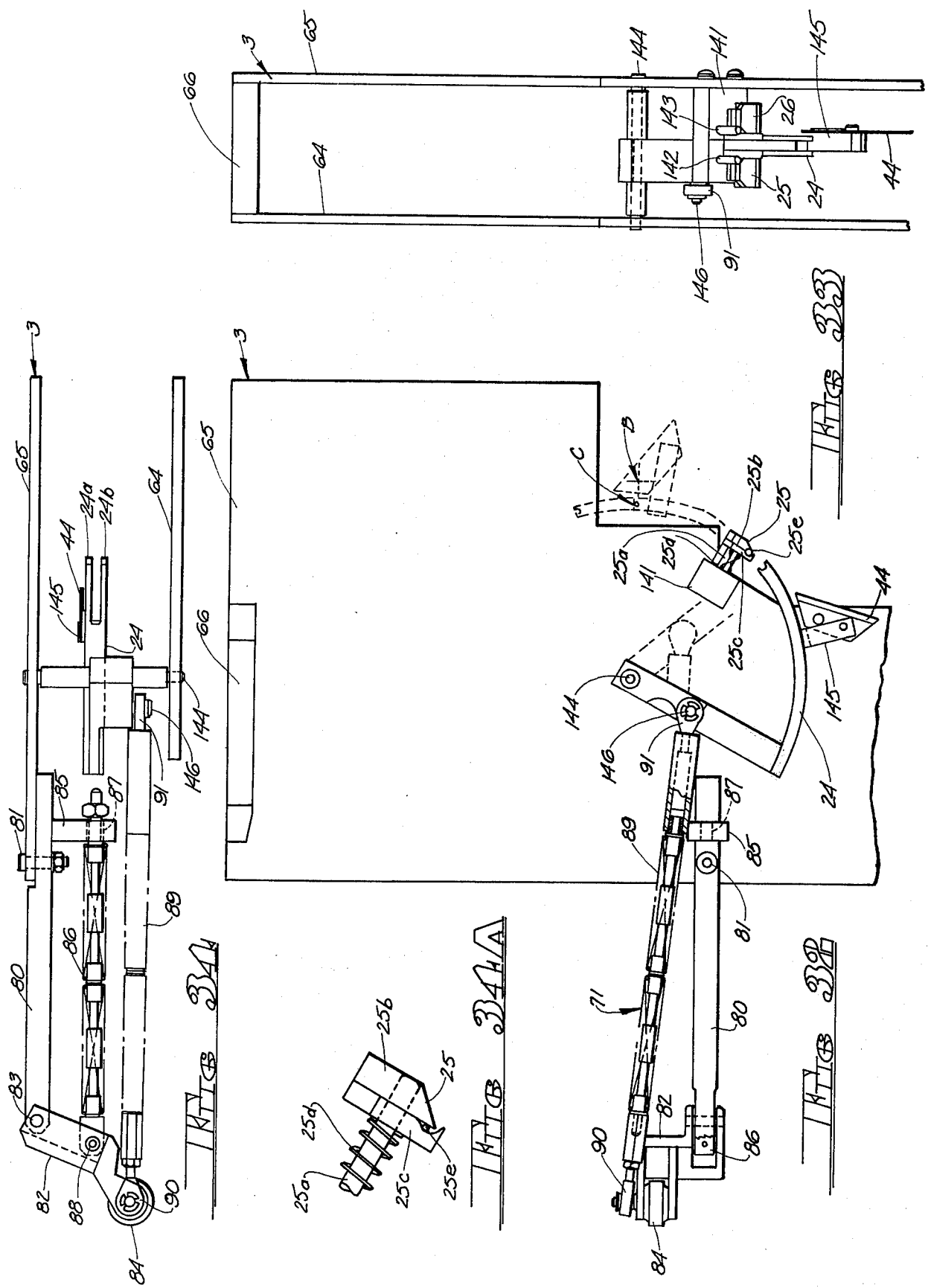

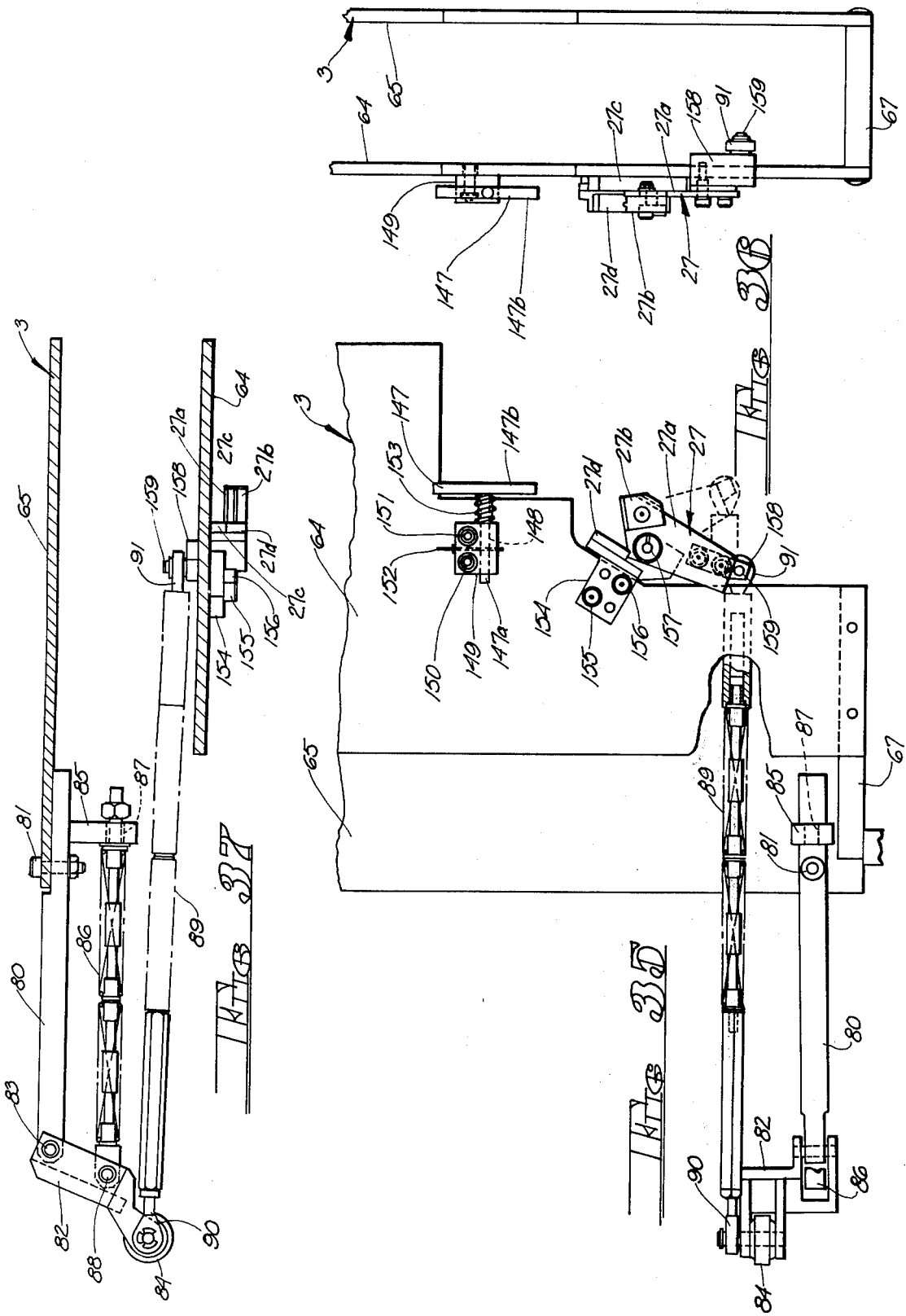

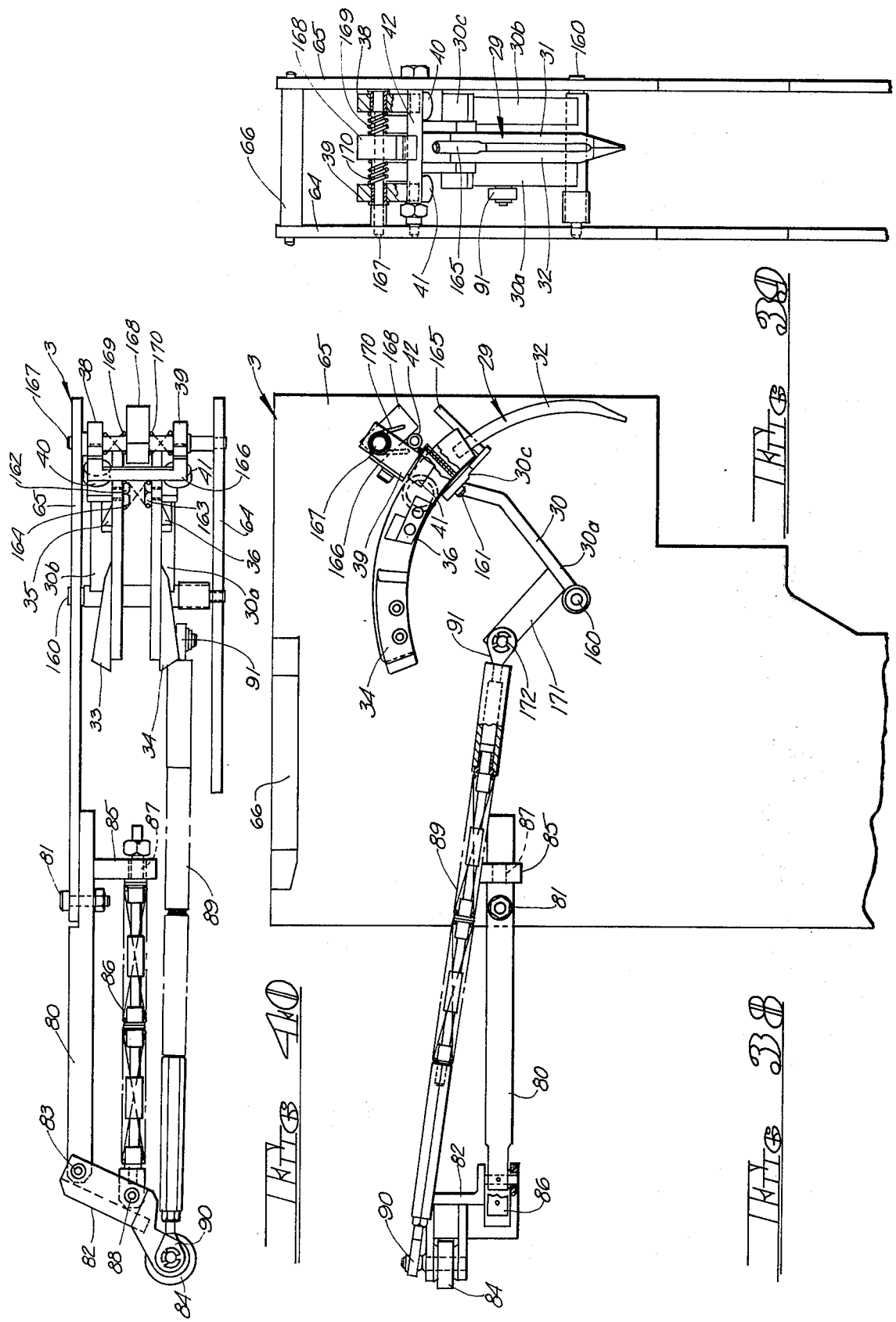

LOOP KNOT TYING METHOD AND APPARATUS

BACKGROUND OF THE INVENTION

1. Field of the Invention

The invention relates to a process and apparatus for forming from string a simple loop knot either through or about a product, and more particularly to a process and apparatus whereby the loop knotting step and other steps may be performed to produce individual products continuously, automatically and at a high production rate.

2. Description of The Prior Art

While the loop knotting process and apparatus of the present invention may have many uses, as will be discussed hereinafter, for purposes of an exemplary showing, they will be described with respect to their application in the manufacture of tampons of the type taught in U.S. Pat. 3,815,601, issued to Jean E. Schaefer on June 11, 1974 and commonly owned by the assignee of the present application. In accordance with the teachings of that patent, the tampon comprises an aggregate composed of individual pieces of absorbent, foam-like material encased within a flexible, fluid-permeable overwrap. The overwrap is in the nature of a tubular sack gathered and sealed at one end, and gathered and closed at the other end by a withdrawal string passed through the gathered overwrap material and formed into a simple loop knot.

Prior art workers have developed numerous knot forming machines for various purposes, as exemplified by U.S. Pat. Nos. 3,166,035 — 3,434,441 and 3,583,131. The knots formed may be complex in nature or very simple utilizing preformed endless loop ties.

For the most part, prior art workers have affixed withdrawal strings to tampons by means of a simple loop knot. In some instances the loop knot has been formed transversely of and around the longitudinal center of a web of absorbent material and the web is thereafter folded upon itself to form a finished tampon. This is taught, for example, in U.S. Pat. Nos. 2,934,068 — 3,011,495 — 3,063,453 and 3,477,102. In other instances the loop knot has been formed through the absorbent material as taught in U.S. Pat. Nos. 3,131,435 and 3,606,643.

Unlike the prior art, however, the apparatus and process of the present invention converts a continuous tube of overwrap material having spaced apart, measured increments of aggregate or like material located therein and glue stripes printed thereon between the spaced, measured increments of aggregate material into individual sacks. Each sack is pleated at its ends. One end of the sack is sealed, while the other end of the sack is gathered and closed by a withdrawal string formed into a loop knot passing therethrough.

The apparatus of the present invention is characterized by remarkable simplicity and a high production rate. The apparatus comprises a rotating drum carrying a plurality of identical heads. Each of the heads is provided with a number of operating instrumentalities performing in sequence the process steps of the present invention. The apparatus operates upon a continuous web or tube of overwrap material and utilizes a single, continuous, external string source.

SUMMARY OF THE INVENTION

In accordance with the present invention a process and an apparatus are provided for forming from string or similar flexible cable-like material a simple loop knot through or about a product. In the exemplary embodiment taught herein, the product comprises a continuous tube of flexible overwrap material having measured increments of foam-like aggregate material within the tube spaced one product pitch apart. Peripheral glue stripes are printed on the tube between the aggregate increments and again one product pitch apart. The purpose of the process and apparatus of the exemplary embodiment taught herein is to form from the tube individual sacks gathered at both ends, sealed at one end and closed at the other end by a withdrawal string loop knotted through the gathered material of that end. Once the sealing and knotting operations have been performed, the tube is cut to form the ultimate sack-like products.

In the exemplary embodiment set forth, the apparatus comprises a rotating drum carrying about its periphery a plurality of identical heads equally spaced from each other. Each head is provided with a pair of pleating jaw assemblies, a pair of clamping jaw assemblies, a pair of string tensioners, a string metering device, a string shear and clamp, a needle to pass a metered length of the string through the tube, spreader-pliers to form the simple loop knot and means to cut the tube into the individual sack-like products.

The heads of the machine are supplied with a single tube which is pulled about the drum by the heads themselves. Similarly, the string for the heads is supplied from a single external string source. As each head rotates with the drum through 360° it is supplied with the tube and the string. Each head first pleats a segment of the tube and then clamps it in pleated condition. One of the clamps engages the tube at the position of a glue stripe and means are provided to heat that clamp to seal the tube at the glue stripe. The string metering device, in cooperation with the string tensioners, meters an appropriate length of string to the needle and the needle engages the string and perforates the tube, carrying the string through the perforation. The spreader-pliers thereafter pass within the string loop formed by the needle and to either side of the needle to engage the free ends of the string, having been cut by the string clamp and shear assembly. The needle is retracted and the spreader-pliers then draws the free ends of the string through the string loop to form the simple loop knot. The tube is thereafter severed and an individual sack, formed from the tube, is suspended by its string from the spreader-pliers and is displayed for pick-up by an appropriate discharge transfer means.

While the invention is described with respect to automatic apparatus having a plurality of identical heads, it is within the scope of the invention to utilize a single head, the operating instrumentalities of which are appropriately actuated. In such an instance, the product tube or individual product elements would be hand-fed to the head or automatically indexed therethrough. It is also within the scope of the invention to cause the loop knot to be formed through a preformed hole in a product. In instances where it is desirable to have a simple loop knot formed around a product, rather than through it, this can be accomplished by causing the needle of the head or heads to pass above the product.

BRIEF DESCRIPTION OF THE DRAWINGS

FIG. 1 is a semi-diagrammatic, fragmentary plan view illustrating the head-carrying drum together with an infeed transfer wheel for the product tube, a discharge transfer wheel for the individual products and an external source of string.

FIGS. 2 through 17 are semi-diagrammatic illustrations of a typical head of the present invention, showing the various operating instrumentalities of the head and the sequence of process steps performed by those operating instrumentalities.

FIG. 18 is a chart illustrating the 360° through which a given one of the heads passes as the drum of the machine rotates and further showing the operation of the instrumentalities of that head during its 360° travel.

FIG. 20 is a fragmentary side elevational view of a typical head.

FIG. 21 is an end elevational view of the head of FIG. 20, as seen from the right in that figure.

FIGS. 22 through 24 are respectively fragmentary side elevational, front elevational and plan views of a typical head of the present invention illustrating the pleating jaw assemblies and the means to actuate them.

FIGS. 25 through 27 are respectively fragmentary side elevational, front elevational and plan views of a typical head illustrating the clamping jaw assemblies thereof and the means to actuate them.

FIG. 28 is a fragmentary auxiliary view, partly in cross section, of the first clamping jaws.

FIGS. 29 through 31 are respectively fragmentary side elevational, front elevational and plan views of a typical head illustrating the needle and needle holder thereof, together with the actuating means therefor.

FIGS. 32 through 34 are respectively fragmentary side elevational, front elevational and plan views of a typical head illustrating the string metering device thereof and its actuating means.

FIG. 34a is a fragmentary side elevational view, partly in cross section, illustrating one of the string tensioners of the present invention.

FIGS. 35 through 37 are respectively fragmentary side elevational, front elevational and plan views of a typical head illustrating the string clamp and shear assembly thereof, together with its operating means.

FIGS. 38 through 40 are respectively fragmentary side elevational, front elevational and plan views of a typical head illustrating the spreader-pliers thereof and its operating mechanism.

FIG. 42 is a semi-diagrammatic illustration similar to FIG. 11 but illustrating the head forming a loop knot around the product rather than through a perforation therein.

DESCRIPTION OF THE PREFERRED EMBODIMENTS

Figure 12:
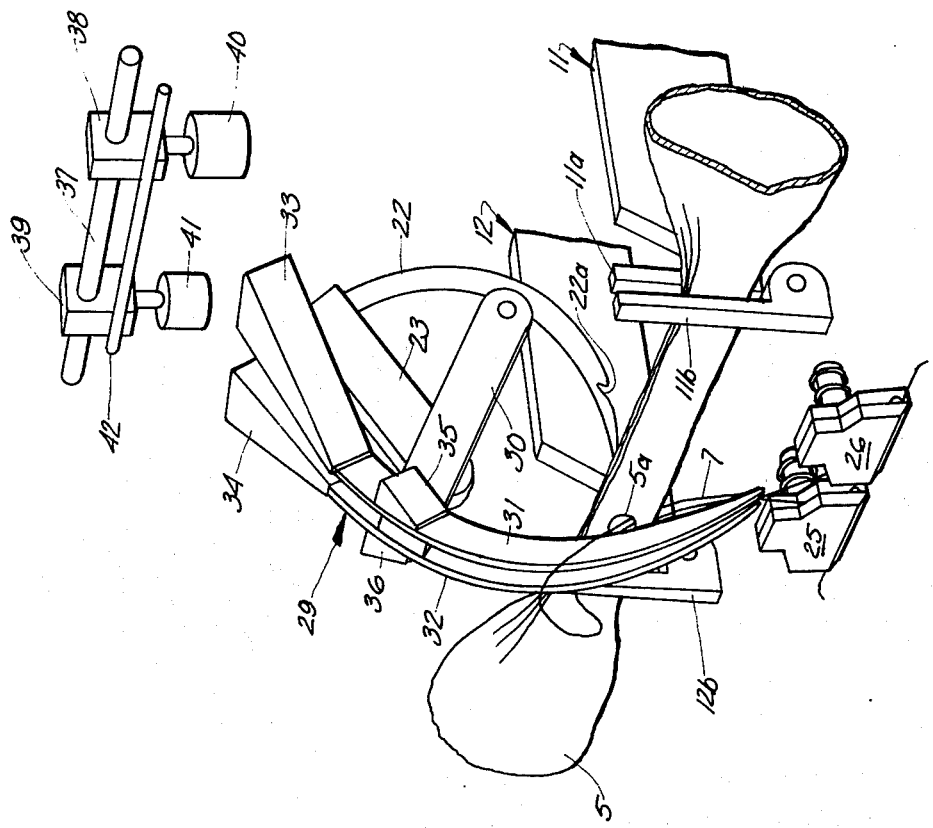

For a better understanding of the process and apparatus of the present invention, the basic steps of the process and the primary operating instrumentalities of the apparatus performing these steps will first be described in association with the semi-diagrammatic representations thereof in FIGS. 1 through 17 wherein like parts have been given like index numerals. Turning first to FIG. 1, the apparatus of the present invention comprises a drum generally indicated at 1. Means (not shown) are provided to rotate the drum about its vertical axis 2 in the direction indicated by arrow A. Evenly spaced about its periphery, the drum carries a plurality of substantially identical heads or stations (some of which are indicated at 3), each made up of six basic operating instrumentalities to be described.

The product materials, in the particular exemplary application of the machine to be described, comprise a continuous tube of flexible material having a substantially circular cross section maintained by separate measured increments of aggregate material located inside the tube and spaced one product pitch from each other. Peripheral glue stripes are also printed on the tube between adjacent increments of aggregate material, again one product pitch from each other. It is the function of each head or station to form from the tube a discrete product comprising a sack-like structure heat sealed at one end closed with a string at the other end and containing one measured increment of aggregate material.

As will be described, the six basic operating instrumentalities of each head are actuated in the proper sequence as the drum rotates by means of fixed plate cams located within the drum. As the drum rotates, each head thereon will perform its various operations within the 270° active portion of the drum cycle indicated in FIG. 1. These operations include pleating and clamping an appropriate portion of the tube, heating the clamping jaws to seal the tube at one of the above mentioned peripheral glue stripes printed thereon, metering the correct length of string to a needle, cutting the string, piercing the pleated tube, forming the string into a simple loop knot passing through the pierced hole and around the side of the tube, cutting the tube to form one sack or product and displaying the finished sack for transfer by its string to a transfer means by which the sack is taken to additional mechanisms for the performance of further operations thereon; these further operations do not constitute a part of the present invention. Similarly, the product discharge transfer means does not constitute a part of the present invention. Any appropriate conveying means may be used. For purposes of an exemplary showing, a discharge transfer wheel is illustrated in FIG. 1 at 4.

The product material or tube (indicated at 5) enters the heads of the drum tangentially from outside the drum. The feed means for the tube does not constitute a part of the present invention and may be any appropriate feed means. For purposes of an exemplary showing, a tube infeed transfer wheel is shown at 6. Each head performs the sealing and loop knotting operations on one product or sack while part of the continuous tube. After these operations, the sacks are cut from the tube to form the individual products shown in FIG. 1 at 5'. In the feeding of the tube to the heads of the drum 1, it is important for this particular product that both the measured increments of aggregate within the tube and the peripheral glue stripes on the tube be kept in registration with the heads.

The string 7, to be formed into a loop knot through each sack product, is pulled into each head in similar fashion to the product tube 5 from one fixed spool outside and tangent to the drum 1. In FIG. 1, three such spools are illustrated at 8, 9 and 10, the string of each spool being tied to the string of the spool ahead of it to minimize or eliminate shutdown for changing or adding additional spools of string. Thus when one spool is depleated, another spool can be installed and its string tied to the immediately preceeding spool.

The drum 1 provides a high speed, continuous operation. The tube 5 and string 7 are, after an initial thread-up, pulled continuously and automatically into each head 3 of drum 1. In a working embodiment of the loop knotting machine of the present invention a rotating drum 1 is provided with 45 operating heads 3 evenly spaced about its periphery. The rotating drum provides 15 feet of active travel for each station, during which time each station performs its various operations on one product.

FIGS. 2 through 16 illustrate the operating instrumentalities of one of the heads 3 of drum 1, it being understood that all of the heads or stations are substantially identical. In FIG. 2, the clamping jaw assemblies and pleating jaw assemblies of the head are shown. A first clamping jaw assembly is generally indicated at 11 and comprises a first clamping jaw 11a and a second clamping jaw 11b. The clamping jaw 11a is adapted to shift axially between open and closed position. The second clamping jaw 11b is arranged to rotate between open and closed positions. In FIG. 2, the clampings jaws 11a and 11b illustrated in their open positions. In closed position, clamping jaws 11a and 11b are in substantial abutment with the tube 5 therebetween. A second clamping jaw assembly is generally indicated at 12 having a first clamping jaw 12a and a second clamping jaw 12b. The clamping jaws 12a and 12b are similar to clamping jaws 11a and 11b and function in substantially the same manner.

In FIG. 2, the product tube 5 is shown provided with a peripheral glue stripe 13. A measured increment of aggregate material is shown within the tube in broken lines at 14.

A first pleating jaw assembly is generally indicated at 15 and comprises an upper pleating jaw 15a and a lower pleating jaw 15b. Upper and lower pleating jaws 15a and 15b are illustrated in their open position. In their closed position, the teeth 16 of upper pleating jaw 15a interdigitate with the teeth 17 of lower pleating jaw 15b with the tube 5 therebetween. A second pleating jaw assembly is generally indicated at 18 and comprises an upper pleating jaw 18a having teeth 19 and a lower pleating jaw 18b having teeth 20. The upper and lower pleating jaws 18a and 18b are substantially identical to upper and lower pleating jaws 15a and 15b and function in the same manner.

The tube 5 is pulled from the positive grip infeed transfer wheel 6 (FIG. 1) into the open clamping jaw assembly and pleating jaw assembly of the head (when the head is tangent to the incoming tube) by closed clamping jaw assemblies in heads further downstream. The pitch line speed of drum 1 carrying the head is perferably slightly faster than the pitch line speed of the infeed transfer wheel 6 in order to maintain some tension in the tube. This tension is desirable to provide consistent location of the tube within the open clamping and pleating jaw assemblies as they close. The direction of drum rotation is indicated by arrow A and the tube 5 is so registered with the heads on the drum that the measured increments of aggregate or like material within the tube are located between the heads and the glue stripes 13 on the tube are located inside the heads in line with the downstream clamping jaw assemblies 11 thereof.

When a head 3 is tangent to the incoming tube 5 and is so positioned as to receive the tube, all of its operating instrumentalities are in their retracted or open position. In FIG. 2, the clamping jaw assemblies 11 and 12 and the pleating jaw assemblies 15 and 18 are shown in such open position.

Pleating jaw assemblies 15 and 18 close first, as illustrated in FIG. 3. The pleating jaw assemblies ripple the tube 5 so as to provide a plurality of layers of the tube material through which the needle (to be described hereinafter) passes the string. By being a part of the head, the pleating jaw assemblies accurately locate these layers of the material of tube 5 for the needle to pierce. Both the upper and lower pleating jaws of pleating jaw assemblies 15 and 18 open and close together, being connected by a four-bar linkage inside the head, as will be described hereinafter. It will further be understood that the pleats formed by the pleating jaw assemblies of each head fall between the increments 14 of aggregate within the tube 5.

Figure 4B:
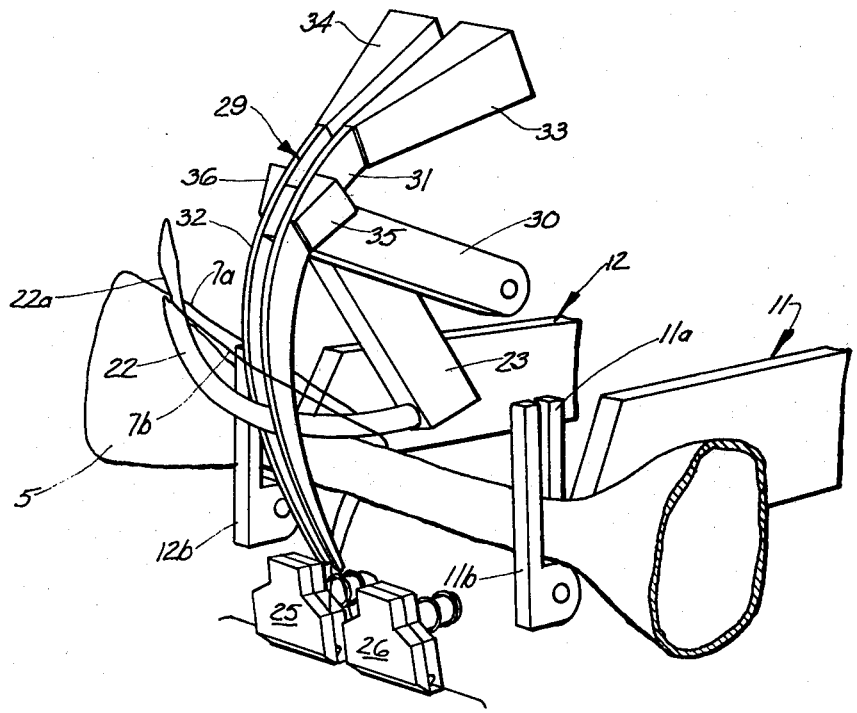

Once the pleating jaw assemblies have formed the pleats in the tube 5, the clamping jaw assemblies, located between the pleating jaw assemblies, close upon the pleated tube. Both jaws of each clamping jaw assembly move so that in their open position they will not interfere with the pleating step. In their closed position, they gather the pleats as is illustrated in FIG. 4. As will be evident hereinafter, the clamping jaw assemblies maintain the pleats throughout the sealing, loop knotting and tube severing steps.

The downstream clamping jaw assembly 11 engages the tube 5 at the position of the peripheral glue stripe 13. This clamping jaw assembly will be used to seal the tube at the glue stripe, as will be seen hereinafter. The other clamping jaw assembly 12 does not have a sealing function. Its purpose is to maintain the pleats and the tension in the tube 5 between the clamping jaw assemblies for the loop knotting operation. Needle piercing force is reduced if the tube is maintained taut. To enable each clamping jaw assembly to engage the pleated tube tightly, the first or slidable jaws 11a and 12a thereof, are independently spring loaded. The two rotating clamping jaws 11b and 12b are mounted on a common pivot shaft connected by a four-bar linkage to the jaws 11a and 12a so that both jaws of each clamping jaw assembly operate together.

Turning to FIG. 5, once the clamping jaw assemblies 11 and 12 have engaged the pleated tube 5, the pleating jaw assemblies 15 and 18 open. This provides clearance about the clamping jaw assemblies for passage thereof through a fixed induction heating coil (generally indicated at 21) mounted externally of the drum 1. The induction heating coil comprises a long, narrow U-shaped structure curved to match the pitch circle about the drum 1. The coil may be of any suitable and well known construction. For example, in a working embodiment of the present invention coil is made up of quarter-inch copper tubing through which cooling water passes. On the outside of the coil a low voltage, radio frequency alternating current is carried. The clamping jaw assemblies 11 and 12 pass between the legs of the U-shaped induction heating means. These legs are diagrammatically illustrated at 21a and 21b in FIGS. 1 and 5.

Only the downstream clamping jaw assembly 11 is intended to provide a sealing function, this clamping jaw assembly engaging the tube 5 at the position of the peripheral glue stripe 13. As a consequence, the abutting portions of clamping jaw assembly 11 are made of a magnetic material. The remaining support portions of clamping jaw assembly 11 and the other operating instrumentalities of the head (including clamping jaw assembly 12) are preferably made of non-magnetic materials such as austenitic stainless steel or the like so that the heating effect of the induction heating coil 21 is confined only to clamping jaw assembly 11. The high frequency oscillating magnetic field generated between the legs 21a and 21b of the induction coil induces heat by magnetic hysteresis loss in the abutting portions of clamping jaw assembly 11 which, in turn, is conducted to that portion of the tube having the glue stripe. The glue stripe melts to form the heat seal.

As is indicated in FIG. 1 the pleating and clamping steps take place during about the first 36° of the active portion of the drum cycle. The sealing step occurs thereafter until the drum has passed through about 120° of its active cycle.

Once the tube 5 has been pleated, clamped and sealed the head functions to meter the correct length of string for its product and to cut the string. Turning to FIG. 6, in addition to the clamping jaw assemblies 11 and 12 a needle 22 and needle holder 23 are illustrated, together with a string metering device 24. A pair of string tensioners are diagrammatically indicated at 25 and 26. A string clamp and shear assembly, mounted on the head, is generally indicated at 27 and comprises a shear blade 27a with a clamping foot 27b affixed thereto together with an anvil 27c cooperating with shear blade 27a and a resilient clamping pad 27d cooperating with clamping foot 27b. A similar clamp and shear assembly is also generally indicated at 28 having a shear blade 28a, a clamping foot 28b, an anvil 28c and a resilient clamping pad 28d. The clamp and shear assembly 28 does not constitute a part of the head illustrated in FIG. 6, but is mounted on the next adjacent downstream head. Again, the direction of rotation of drum 1 (i.e. the direction of movement of the head) is illustrated by arrow A.

In actuality, during the running of the loop knot forming machine of the present invention, the string may pass through several heads, being drawn therethrough by a closed clamp and shear assembly of a head further downstream. This allows several string metering devices to be active at once to provide slower, mor gentle string handling. For purposes of explanation, however, the string 7 in FIG. 6 is shown as being drawn into the head from the spool 8 by the clamp and shear assembly 28 of the next adjacent downstream head. As the string enters the head, it also enters the pair of tensioners 25 and 26, as shown in FIG. 6.

When the string is properly positioned as in FIG. 6, the string metering device 24 rotates upwardly toward the needle 22, intersecting the string stretched between the tensioners 25 and 26. The string metering device comprises bifurcations 24a and 24b, the free ends of which are notched as at 24c and 24d, respectively. As is clearly shown in FIG. 7, the string metering device 24 engages the string between tensioners 25 and 26 in its notches 24c and 24d. As it moves upwardly, string will be drawn through tensioner 25 from the spool 8. As the string metering device 24 approaches its uppermost string metering position, the needle 22 and its holder 23 will rotate toward the pleated tube 5, passing between bifurcations 24a and 24b of the string metering device. This movement of the needle causes the string 7 to be engaged in a notch 22a in the needle near its point.

At the end of the metering stroke of the string metering device 24, the correct length of string has been established between the string clamp and shear assemblies 27 and 28. It will be noted that the correct length of string is greater than the pitch length of each product. The string metering device 24 and tensioners 25 and 26 cooperate to provide this additional string length. In order to complete the loop knot forming step, the free end of string 7 held by string clamp and shear assembly 28 must be released and the spool end of string 7 must be cut by string clamp and shear assembly 27. Since only one clamp at a time is pulling the string off spool 8, the spool end of the string must be cut and thereby clamped by string clamp and shear assembly 27 before the free end of the string can be unclamped by string clamp and shear assembly 28. This is illustrated in FIG. 8.

Turning now to FIG. 9, once the ends of that segment of string 7 utilized by the head have been released, the needle 22 can begin its rotation through the pleated tube 5. The needle will pierce the pleated tube and carry the string with it in the needle notch 22a. The string metering device 24 does not retract until the needle notch has carried the string through the pierced hole 5a in the pleated tube so that the friction from the hole edges will prevent the string from slipping out of needle notch 22a. Thereafter, the string metering device 24 will retract from between string tensioners 25 and 26 prior to the time the needle 22 completes its stroke, so that the final needle motion will pull tension on the string between the hole and the tensioner disks. FIG. 9 illustrates the needle 22 in its extended position and the string metering device 24 in its retracted position.

FIG. 10 illustrates the spreader-pliers mounted in the head. The spreader-pliers is generally indicated at 29 and comprises an actuator 30 to which a pair of arcuate jaws 31 and 32 are pivotally attached in such a way that their ends may shift toward and away from each other. The rearward ends of jaws 31 and 32 bear large cam elements 33 and 34 and small cam elements 35 and 36, respectively. A non-rotating shaft 37 is fixed within the head. A pair of blocks 38 and 39 are supported by shaft 37 and are mounted for rotation thereon. The blocks 38 and 39 support cam wheels 40 and 41. While not shown in FIG. 10, means are provided in association with the jaws 31 and 32 to urge the forwardmost pointed ends thereof into abutment. This biasing means in association with the spreader-pliers jaws will be described hereinafter. Nevertheless, it will be evident from FIG. 10 that if the actuator 30 is rotated in a counter-clockwise direction as viewed in FIG. 10, the large cam elements 33 and 34 will cooperate with the cam wheels 40 and 41, respectively, to cause the pointed ends of the pliers jaws to spread apart. As the actuator 30 rotates to the extent that cam elements 33 and 34 pass beyond cam wheels 40 and 41, the above mentioned biasing means will cause the pointed ends of the pliers to snap together. The purpose of small cam elements 35 and 36 will be described hereinafter. A stop bar 42 prevents blocks 38 and 39 from rotating out of the path of large cam elements 33 and 34 during counterclockwise rotation of the spreader-pliers.

The simplicity of the loop knotting concept of the present invention is based upon the chordal display of the segments 7a and 7b of string 7 across the circular arc of the curved needle 22 as seen in FIGS. 9 and 10. As illustrated in FIG. 10, when the needle 22 has reached its forwardmost position the spreader-pliers 29 may begin its downward movement. As the jaws 31 and 32 pass between the string segments 7a and 7b the jaws will be spread by the cooperation of large cam elements 33 and 34 and cam wheels 40 and 41. Jaw 31 will therefore pass between string segment 7a and needle 22, while jaw 32 will pass between string segment 7b and needle 22. Continued downward movement of the spreader-pliers will disengage large cam elements 33 and 34 from cam wheels 40 and 41, respectively, causing the forwardmost ends of the spreader-pliers to snap together, engaging the free ends of string 7. Thus, the spreader-pliers accomplishes two vital functions. It first enters and spreads the loop of string 7 formed by needle 22 and thereafter engages and grips the free ends of the string near tensioners 25 and 26. The tensioners serve to position the string ends for proper gripping by the spreader-pliers.

As soon as the string ends have been gripped by the spreader-pliers 29, the needle retracts as shown in FIG. 12. Thereafter, the spreader-pliers 29 is free to retract with its ends closed and still gripping the ends of string 7.

Figure 13:
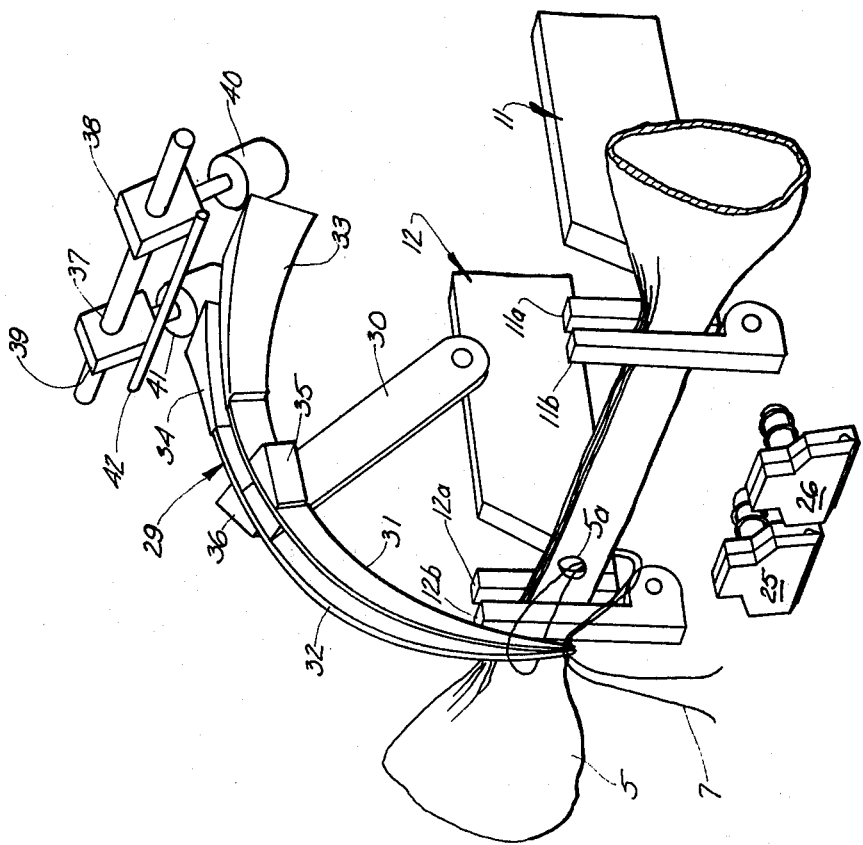

As is shown in FIG. 13, the spreader-pliers 29 will retract with its forwardmost ends closed and gripping the ends of string 7. This means that the large cam elements 33 and 34 at the opposite ends of pliers jaws 31 and 32 will be fully separated from each other. As the large cam elements 33 and 34 move toward cam wheels 40 and 41, they will abut these cam wheels and push them out of the way by virtue of the rotatable mounting of the blocks 38 and 39 on shaft 37 in the head. This is clearly shown in FIG. 13. Means (not shown in FIG. 13, but to be described hereinafter) are provided to bias the cam wheels to the position shown in FIG. 10 (with blocks 38 and 39 against stop bar 42) and to cause them to return to that position as soon as cam wheels 40 and 41 have been cleared by the large cam elements 33 and 34 on the spreader-pliers. As the spreader-pliers retracts, it pulls the string ends through the loop to form a simple side loop knot 43, as is shown in FIG. 14.

Once the knot 43 has been completed, the knotted and sealed tube 5 between clamping jaw assemblies 11 and 12 must be severed before the clamping assemblies can open to release the individual product sack for transfer by the discharge transfer wheel 4. The tube 5 is cut by a blade 44 mounted to one side of the string metering device 24, as illustrated in FIG. 15. The string metering device is caused to rotate a second time to perform the severing step. During the performance of the severing step, the string metering device 24 is rotated further than during its string metering function. Once severing has been accomplished, the string metering device 24 immediately retracts to allow the clamping jaw assemblies 11 and 12 to open and release the sack ends, as is shown in FIG. 16. It will be understood that tube portion 5b in FIG. 16 represents the trailing part of the downstream sack sealed by the head. The seal is shown at 13a. The tube portion 5c in FIG. 16 represents the leading portion of that sack product tied by the head. It will be noted that had the sack severing blade 44 been mounted between clamping jaw assembly 12 on the other side of needle 22 and the needle, and had clamping jaw assembly 12 been the heated one, then the sealed end of a sack would have led the knotted end around the drum 1.

As the tubing or bag portions are released by clamping jaw assemblies 11 and 12 the spreader-pliers 29 again rotate forwardly to the extend that the cam wheels 40 and 41 engage the small cam elements 35 and 36 to spread the pliers tips slightly, releasing the grip thereof on the string 7. This movement of the spreader-pliers 29 not only positions the tips thereof in an open area below the upper pleating jaws 15a and 18a (see FIG. 2) so that the discharge transfer wheel 4 can grip the string as close to the pliers tips as possible, but also releases the string from the pliers tips as the discharge transfer wheel gains control of the string so as to prevent the string from having to be forceably pulled from the pliers tips which would cause the string ends to become frayed. The removal of the product by the discharge transfer wheel is shown in FIG. 17. Thereafter, the spreader-pliers returns to its fully retracted position.

Figure 18:
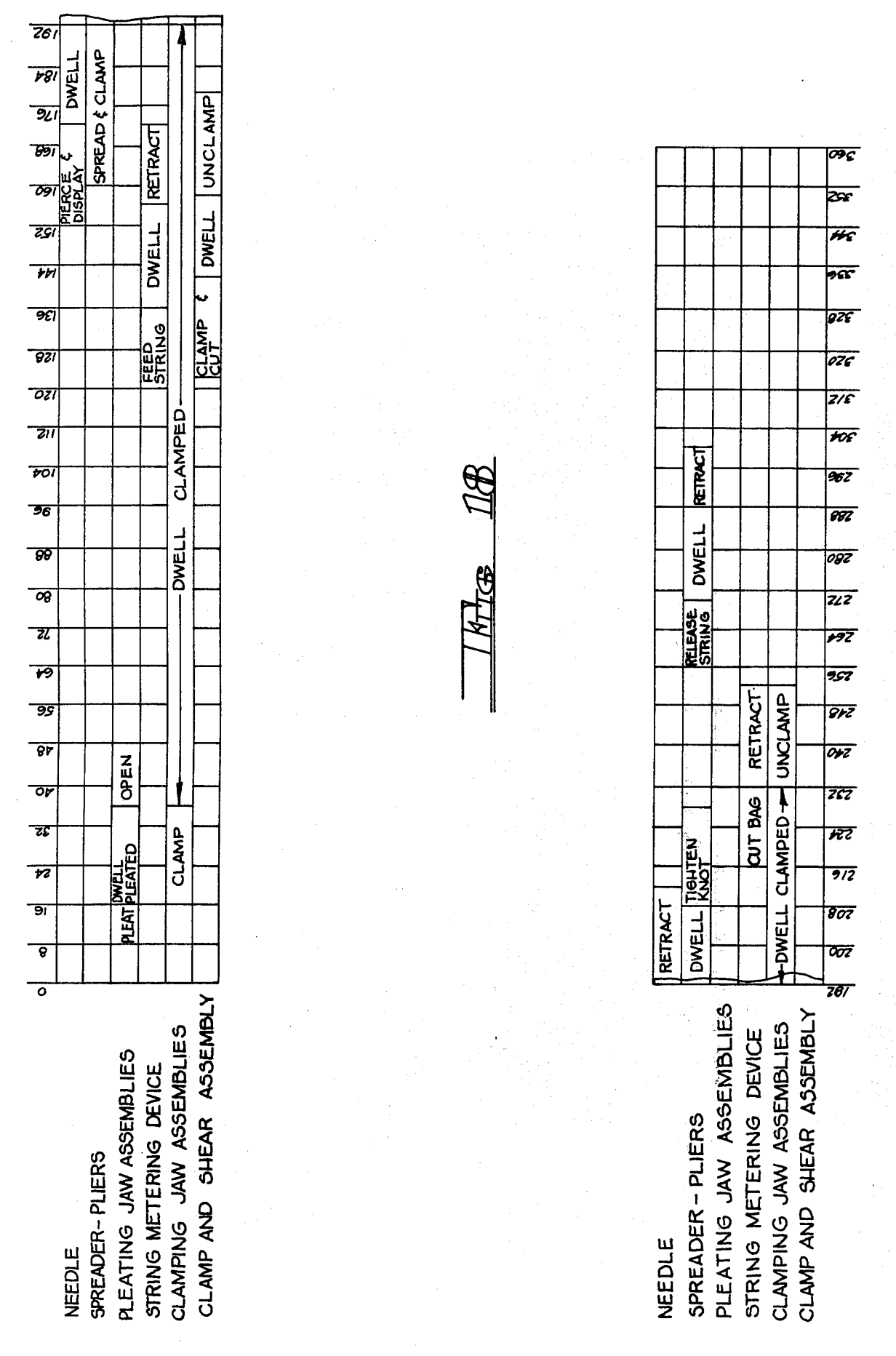

Having described the various steps performed by the six operating instrumentalities of the head, reference is made to FIG. 18 which graphically illustrates the 360° travel of the head and the sequence of these steps. The zero degree vertical line at the left of the chart corresponds to the zero degree line of FIG. 1. At the left the chart lists the six operating instrumentalities of each head. The sequence may again be considered in terms of a single one of the heads, since all of the heads function in the same manner.

The first operating instrumentality listed is the needle 22. Thus, as the drum 1 rotates and the head reaches its 152° position, the needle will begin to move from its retracted position. From 152° to 172° the needle will pierce the pleated tube 5 and display the string segments 7a and 7b. From 172° to 192° the needle will remain in its extended-most position. From 192° to 212° the needle will retract and will remain retracted until the head again reaches its 152° position wherein the cycle will repeat.

The spreader-pliers 29 will shift past the small and large cam elements 35–36 and 33–34 as the head passes between 160° and 192° from its starting point. Between 172° and 192°, the spreader-pliers will spread, by virtue of the large cam elements 33 and 34, as it passes between the string segments 7a and 7b and will then engage the free ends of the string. It will thereafter remain in the extended position until the head reaches a position of 208° to allow the needle to retract. From 208° to 228° the spreader-pliers will fully retract to tighten the knot 43. The spreader-pliers will remain in its fully retracted position until the head reaches 256°. From 256° to 270°, the spreader-pliers will shift forwardly to the extent that the small cam elements 35 and 36 will cause it to release the string ends. The pliers will remain in this position until the head reaches 288°, whereupon between 288° and 300° the pliers will fully retract and remain so until the next cycle begins.

The pleating jaw assemblies 15 and 18 close upon the tube 5 as the head passes between its 8° and 16° positions. Between the 16° and 36° positions of the head, the pleating jaw assemblies maintain the tube 5 in pleated condition. Between 36° and 48°, the pleating jaw assemblies return to their retracted positions. The pleating jaws remain fully retracted for the remainder of the cycle.

The chart of FIG. 18 illustrates both movements of the string metering device 24. From the 120° to the 136° positions of the head, the string metering device meters the string between the string tensioners 25 and 26. From 136° to 156° the string metering device maintains its metering position and then fully retracts between 156° and 172°.

As the head reaches 216°, the string metering device again comes into play, achieving its fully extended tube cutting position at 232°. From 232° to 252°, the string metering device fully retracts, to remain fully retracted until the next cycle.

The clamping jaw assemblies 11 and 12 clamp the tube 5 between the 16° and the 36° positions of the head. These assemblies remain in their clamped position until they retract between the 232° and the 252° positions of the head. It will be noted that clamping jaw assembly 11 is heated between the 64° and the 124° positions of the head.

Finally, the clamp and shear assembly 27 mounted on the head will clamp and cut the string 7 between the 122° and 142° positions of the head. The assembly will remain in its clamping position until the 158° position of the head. From 158° to 178° the assembly will open.

A comparison of FIG. 1 and FIG. 18 will show that all operating instrumentalities of the head are open to receive material in the area between the infeed transfer wheel 6 and product discharge transfer wheel 4. As indicated above, the clamping jaw assemblies 11 and 12 of each head pull the tube 5 about the drum. However, since the clamping jaw assemblies of each head do not fully close until the head reaches 36° past the infeed transfer wheel 6, the operator cannot reach the first closed clamp in order to secure a starting end of the tube 5 to the machine. As a consequence, the pleating jaw assemblies, which close much closer to the infeed transfer wheel 6, (at the 16° position of each head) may be used for manual thread-up of the tube 5.

Ejection means is required for removing product sacks which are not transferable because of the absence of string. Any appropriate ejection means including a rotating brush may be employed and should be located between the discharge transfer wheel 4 and the infeed transfer wheel 6.

The pitch of each machine head is a fixed dimension. However, the pitch of the glue stripes 13 on the tube 5 may vary slightly with the tension imparted to the tube or the size of the increment of aggregate material in the tube. As a consequence, adjustment means should be provided to assure appropriate positioning of the glue stripes on the tube with respect to the heads. For example, running tension adjustment means may be provided in association with the infeed transfer wheel 6. Such means are well known in the art and do not fall within the scope of the present invention. To compensate for a change in the product pitch length, other appropriate adjustment means must be provided. For example, each head may be provided with a pitch bar (to be described hereinafter) which intersects the chord of the tubing that stretches from clamping jaw assembly to clamping jaw assembly between adjacent heads and which is adjustable radially to change that chord length. It is important that the same adjustment be made between all adjacent heads.

The string supply illustrated in FIG. 1 comprises a number of spools. In the exemplary showing, three spools 8, 9 and 10 are illustrated. These spools are fixed and string unwinds from one spool at a time without spool motion. Since all of the string on a given spool is outside the core thereof, the inner string end of one spool can be tied to the outer or lead end of the adjacent spool. In this way an infinitely long, continuous string source may be provided.

The advantages of such a string supply, as opposed to one that involves a separate spool rotating with each head, lies in the fact that only one spool at a time is being used. There is no shut-down required to replenish and thread-up a string supply for each head on the drum 1. There is only one string supply to fail, and when it does, it can be immediately detected. The string supply arrangements eliminates string waste and requires very little space.

Initial thread-up of the string is accomplished when the machine is stationary. The lead end of the string 7 is provided with a loop which may be hooked over a pin (not shown) extending from the clamp and shear assembly of the head nearest the operator. When the machine is started, the free end of the string remains looped to the pin and is pulled around the machine. Eventually the clamp and shear assembly 27 of that head will close to simultaneously cut and clamp the string. The severed portion of the string will ultimately fall away and will not interefere with the string feeding of succeeding cycles.

It is important that the string remain taut, so that it properly seats in head tensioners 25 and 26. As a consequence, any appropriate and well known tensioning means may be provided in association with the string supply.

It is also within the scope of the invention to provide additional sensing means (not shown) to sense a broken string and to sense a knot in the string, including splice knots. Although the mechanisms of the heads will not be damaged by small splice knots, nor will the knot snag and interrupt the string feed, nevertheless, there is a possibility that a knot will provide more drag in one or the other of tensioners 25 and 26 after the string has been cut during the knot forming operation. This, in turn, may result in a product with excess offset between string ends. Such a product can be automatically rejected at the discharge transfer wheel if the knot detector signals a memory device (not shown), as is well known in the art, so that the product in question can be rejected. The memory device provides a reject signal when the corresponding product arrives at the discharge transfer wheel 4.

Figure 19:
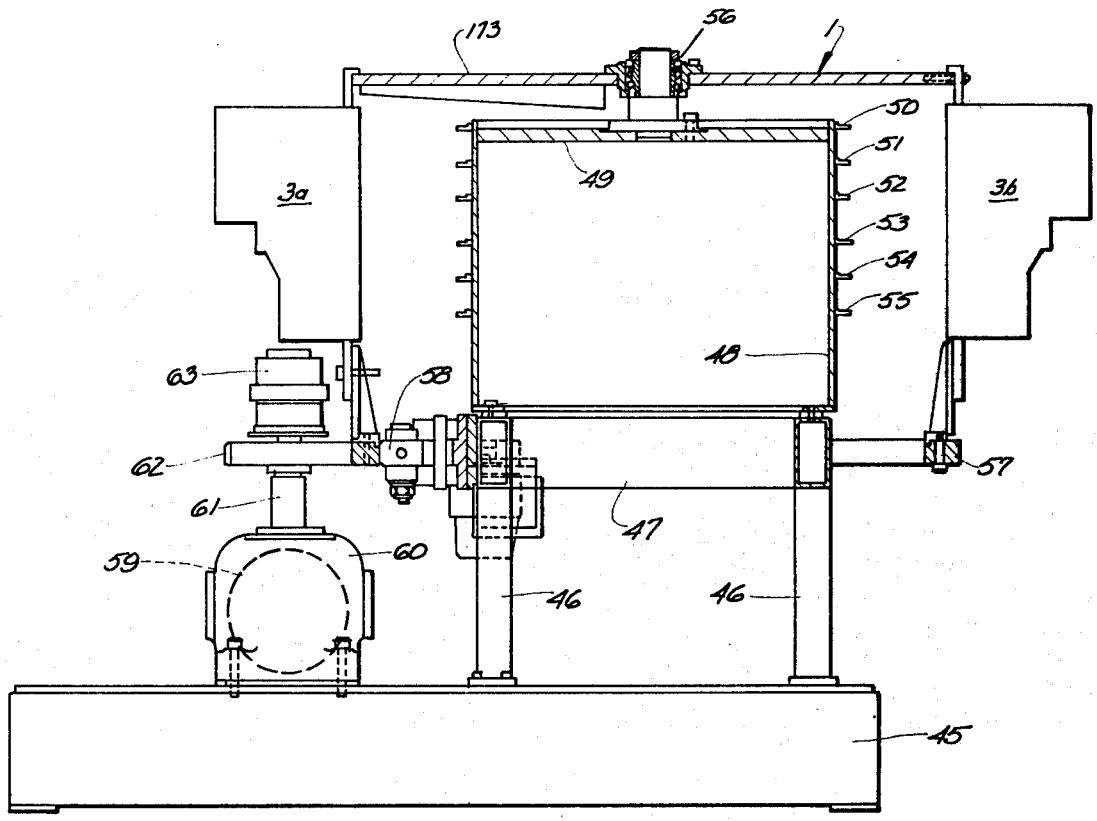
FIG. 19 is a simplified side elevational view of the loop knotting machine, partly in cross section.

Having described the basic suturing machine and the six primary operating instrumentalities of each of its heads, reference is made to FIG. 19 wherein the machine itself is shown, partly in cross section. The machine comprises a suitable base 45 upon which a number of vertical supports or legs are mounted, two of which are shown at 46. These legs, in turn, support a horizontal frame 47 surmounted by a cylindrical member 48 having a top portion 49. The cylindrical member 48 is stationary and carries about its periphery six cam surfaces shown at 50 through 55. Cam surface 50 actuates the needle 22 of each head. Cam 51 operates the spreader-pliers 29 of each head. Pleating jaw assemblies 15 and 18 of each head are activated by cam 52, while the string metering device 24 of each head is governed by cam 53. Cam 54 controls the clamping jaw assemblies 11 and 12 of each head and the clamp and shear assembly 27 of each head is controlled by cam 55.

The drum 1 includes a top plate 173 which is supported for rotation by thrust bearing 56. The top plate 173, in turn, supports the heads of the machine, two of which are shown at 3a and 3b. The heads, themselves, support a ring gear 57 at their lowermost edges. The top plate 173, heads and ring gear 57 are combined to form the hollow drum 1 having its upper end closed and its lower end open. The drum 1 is maintained in the proper attitude by three radial bearings evenly spaced about the frame 47. One such radial bearing is illustrated at 58.

The drum 1 is driven by a motor 59 connected to a gear box 60. The output shaft 61 of gear box 60 carries an input pinion 62 which is in engagement with the ring gear 57. The output shaft 61 may also support drive means 63 for the tube infeed transfer wheel 6 (shown in FIG. 1).

FIGS. 20 and 21 are, respectively, fragmentary side elevational and front elevational views of a typical head. It will be remembered that all of the heads of the loop knotting and sealing machine are identical. For this reason, the head of FIGS. 20 and 21 may be assumed to be the same as the head shown in FIGS. 2 through 17 and is generally indicated by index numeral 3. The head comprises a pair of plates 64 and 65 held in parallel spaced relationship by spacing means, two of which are shown at 66 and 67.

FIGS. 20 and 21 illustrate the needle 22 and its actuating mechanism generally indicated at 68 in abutting relationship with stationary cam 50. The spreader-pliers 29 and its operating mechanism, generally indicated at 69, are shown together with stationary cam 51. Stationary cam 52 is shown in conjunction with the operating mechanism (generally indicated at 70) for the pleating jaw assemblies 15 and 18. In similar fashion, the string metering device 24 is shown operatively connected to its actuating mechanism generally indicated at 71 and in abutment with stationary cam 53. Clamping jaws 11a and 11b of clamping jaw assembly 11 and clamping jaws 12a and 12b of clamping jaw assembly 12 are shown, together with their actuating mechanism generally indicated at 72 and the stationary cam 54. Clamp and shear assembly 27 is shown together with its actuating mechanism (generally indicated at 73) and stationary cam 55. FIGS. 20 and 21 also illustrate tensioners 25 and 26 and blade 44. The center line of that portion of tube 5 which would be located within the head 3 is indicated at B.

FIGS. 22 through 24 illustrate the pleating jaw assemblies 15 and 18 and their operating mechanism 70. As is most clearly seen in FIGS. 23 and 24, upper pleating jaws 15a and 18a comprise a unitary U-shaped element non-rotatively affixed to a shaft 74 by cap screws or the like 75 and 76. The shaft 74 is rotatively supported by the side plates 64 and 65 of the head 3. In similar fashion (see FIG. 23) the lower pleating jaws 15b and 18b comprise a unitary U-shaped structure non-rotatively mounted to a shaft 77 by cap screws 78 and 79. Shaft 77 is rotatively supported by the head side plates 64 and 65.

An elongated support 80 extends rearwardly of the head 3 and is affixed to side plate 65 by bolt means, one of which is shown at 81. A swing arm bracket 82 is pivotally affixed to the support 80 as at 83. The swing arm bracket carries a follower wheel 84 adapted to contact stationary cam surface 52 (see FIGS. 19 and 20). An additional bracket 85 is mounted on side plate 65. One end of a guide rod 86 passes freely through a perforation 87 in the bracket 85. The other end of the guide rod 86 is pivotally affixed to the swing arm bracket 82 as at 88. The guide rod 86 is provided with springs 86a and 86b. These springs urge the pivoted end of the guide rod away from the bracket 85 through which the guide rod slides. This, in turn, assures that the follower wheel 84 will remain in contact with stationary cam 52.

An actuating rod 89 is provided with a rod end 90 pivotally affixed to the swing arm bracket. The other end of the actuating rod 89 has a rod end 91 pivotally affixed to an upper pleater crank 92, to be described hereinafter. The actuating rod 89 is provided at one end with a hollow tubular portion 89a. The central portion of the actuating rod comprises a shaft 89b adapted to be telescopically received in the portion 89a. Spring members 89c and 89d maintain the shaft 89b in its extended position as shown in FIG. 22. This construction enables the actuating rod 89 to telescope, effectively shortening its length should, for any reason, the pleating jaw assemblies 15 and 18 become jammed. This, in turn, will prevent damage to the various parts. Normally, actuating rod 89 will be in its fully extended condition as illustrated in FIGS. 22 and 24 and is preloaded by captive springs 89c and 89d.

As indicated above, the rod end 91 is pivotally affixed to upper pleater crank 92 as at 93. Upper pleater crank 92 is non-rotatively affixed to shaft 74.

Upper pleater crank 92 is also pivotally joined at 94 to one end of a link 95. The other end of link 95 is pivoted, as at 96 to a lower pleater crank 97. Lower pleater crank 97 is non-rotatively affixed to shaft 77.

The operation of the pleating jaw assemblies will be evident from FIGS. 22 through 24. As stationary cam 52 causes swing arm bracket 82 and follower wheel 84 to pivot about pivot point 83 in a counter-clockwise direction, actuating rod 89 will shift forwardly (to the right as viewed in FIG. 22). This, in turn, will cause upper pleating jaws 15a and 18a to swing downwardly, by virtue of upper pleater crank 92. Simultaneously, link 95 and lower crank 97 will be shifted to the left in FIG. 22, causing the lower pleating jaws 15b and 18b to move upwardly. The pleating jaws meet at the center line B of tube 5, as shown in broken lines in FIG. 22.

All of the remaining five operating instrumentalities of head 3 are provided with a support 80, a swing arm bracket 82, a follower wheel 84, a bracket 85, a guide rod 86 and a telescoping actuating rod 89 substantially identical to those described with respect to FIGS. 22 and 24. For this reason, in the remaining figures like parts have been given like index numerals and do not require further description.

FIGS. 25 through 28 illustrate clamping jaw assemblies 11 and 12 and their operating mechanisms. Second or lower clamping jaws 11b and 12b are non-rotatively affixed to a shaft 99, rotatively mounted in side plates 64 and 65. The second clamping jaws 11b and 12b are held in place by cap screws 100 and 101.

The rod end 91 of actuating rod 89 is pivotally affixed as at 102 to one end of a lower crank 103. The other end of crank 103 is non-rotatively affixed to shaft 99. It will be evident that as stationary cam surface 54 causes actuating rod 89 to move forwardly, crank 103 and shaft 99 will rotate in a counter-clockwise direction (as viewed in FIG. 25) causing the second clamping jaws 11b and 12b to rotate upwardly to their clamped position illustrated in broken lines in FIG. 25.

As is most clearly shown in FIGS. 25 and 28, first or upper clamping jaws 11a and 11b are affixed to block-like structures 104 and 105, respectively. As is most clearly shown in FIG. 28, blocks 104 and 105 are mirror images of each other. A third block is shown at 106.

Block 105 has a central passage 107 therethrough. Block 106 has a coaxial passage 108. A tubular bushing 109 passes through passages 107 and 108. The bushing is held in place by a flange 110 at its rearward end and by a screw 111 passing through the forward end of block 105 and threadedly engaged in the forward end of the bushing The block 105 is spaced slightly forwardly of block 106 and is maintained in this spaced relationship by compression spring 112. Block 104 is of similar construction including bushing 113 passing through block 106 and into block 104 and compression spring 114.

A pair of guide rods 115 and 116 are supported by a bracket 117 mounted on side wall 65 of head 3. The free ends of guide rods 115 and 116 are located in bushings 113 and 109 respectively. Blocks 104, 105 and 106 form a structure longitudinally slidable on guide rods 115 and 116. In this way first or upper clamping jaws 11a and 12a can be shifted between their clamping and retracted positions and guide rods 115 and 116 maintain them in their proper orientation. A plate 118 is mounted on block 106 and prevents rotation of block 105 about guide rod 116. A second plate 119 is fastened to head side plate 65 by screws 120 and 121 and serves to prevent rotation of block 104.

In addition to being shiftable with respect to guide rods 115 and 116, the blocks 104 and 105 can slide on the outsides of their respective tubular bushings 113 and 109 toward and away from block 106. The amount of this movement of block 105 is limited by compression spring 112 and screw 111 (see FIG. 28). The movement of block 104 is similarly limited. Nevertheless, this construction results in the effective independent spring loading of blocks 104 and 105 and the clamping jaws 11a and 12a thereon assuring that clamping jaws 11a and 12a will seat with equal force against rotatable clamping jaws 11b and 12b respectively.

The block 106 has a rearward extension 122 (see FIGS. 25 and 26) pivotally connected as at 123 (see FIG. 28) to one end of a link 124. The other end of link 124 is pivoted as at 125 to a lever 126 non-rotatively mounted on a shaft 127. The shaft 127 is rotatively supported by side plates 64 and 65. An upper crank 128 is non-rotatively affixed to the shaft 127. One end of a link 129 is pivotally joined to crank 128 as at 130. The other end of link 129 is pivotally affixed as at 131 to lower crank 103.

It will be evident that as actuating rod 89 causes lower crank 103 to rotate in a counter-clockwise direction (as viewed in FIG. 25) to bring the second or lower clamping jaws 11b and 12b to their clamping positions, the link 129 will similarly cause clockwise rotation of upper crank 128, shaft 127 and lever 126. This movement of lever 126 will, through the agency of link 124, causes the first or upper clamping jaws 11a and 12a to shift longitudinally to their clamping positions, as shown in broken lines in FIG. 25. As actuating rod 89 is permitted to shift to the left as viewed in FIG. 25, the second clamping jaws 11b and 12b will rotate to their open positions and the first or upper clamping jaws 11a and 12a will shift to their open positions.

FIGS. 29 through 31 illustrate the needle 22 and its operating mechanism. Needle holder 23 is non-rotatively affixed to a shaft 132 which, in turn, is rotatively mounted between side plates 64 and 65. Needle 22 is removably and replaceably mounted on needle holder 23 by a clamping plate 133, held in place by screws, two of which are shown in FIG. 31 at 134 and 135.

While not required, the needle 22 is preferably of triangular cross section, as shown in FIG. 30. As explained heretofore, the needle pushes the string 7 through the tube 5 just after piercing the tube. The triangular cross section of the needle provides the necessary strength of the needle notch 22a while minimizing the size of the hole 5a pierced in the tube 5. It also helps to guide the spreader-pliers 29 as they pass the needle, should they come in contact with the needle. Furthermore, the triangular cross section of the needle assists the string segments 7a and 7b to achieve their chordal position and it maximizes the spread between the needle and string segments 7a and 7b for entrance therebetween of the spreader-pliers.

The shaft 132 carries a pinion 136. This pinion is engaged by a segment gear 137 affixed to a crank arm 138. Crank arm 138 is non-rotatively affixed to a shaft 139. The shaft, itself, is rotatively mounted between side plates 64 and 65. The uppermost end of crank arm 138 is pivotally joined to the rod end 91 of actuating rod 89, as at 140.

Referring to FIG. 29, the crank arm 138 and needle 22 are shown in their fully retracted positions. It will be evident that as the actuating rod 89 is caused to move to the right (as viewed in FIG. 29) by stationary cam surface 50 (see FIG. 20) the crank arm 138 and shaft 139 will rotate in a clockwise direction. This, in turn, will cause a counter-clockwise rotation of pinion 136, shaft 132, needle holder 23 and needle 22. The forwardmost position of needle 22 is shown in broken lines in FIG. 29.

FIGS. 32 through 34 illustrate the string metering device 24 and its operating mechanism, together with string tensioners 25 and 26. Turning first to FIGS. 32, 33 and 34a, the string tensioners are substantially identical and are mounted on a block 141. As is most clearly seen in FIGS. 32 and 34a, string tensioner 25 comprises a rod-like element 25a having fixed at its end a downwardly depending member 25b. A plate 25c is captively and slidably mounted on the rod 25a and is urged against the downwardly depending member 25b by a spring 25d. The plate 25c and the downwardly depending member 25b define a notch 25e for receipt of the string 7.

Affixed to string tensioners 25 and 26 there is a pair of guide pins 142 and 143 (see FIG. 33) which tend to bring the string ends closer together to minimize the distance required between the pliers tips when open.

The string metering device 24 is non-rotatively affixed to a shaft 144, rotatively supported between side plates 64 and 65. The string metering device 24 carries a bracket 145 to which is replaceably mounted the blade 44.

The forward rod end 91 of actuatingg rod 89 is pivotally attached to the string metering device 24 as at 146. When the actuating rod 89 is shifted to the right (as viewed in FIG. 32) by stationary cam surface 53 (see FIG. 20) the string metering device and shaft 144 will be caused to rotate in a counter-clockwise direction. In FIG. 32 the string metering device is shown in full lines in its retracted position. In broken lines, the string metering device is shown in its fully extended position (i.e. the position achieved when blade 44 cuts tube 5). The position achieved by the string metering device during its metering operation is indicated by arrow C.

FIGS. 35 through 37 illustrate the string clamp and shear assembly 27 of FIG. 6, together with its actuating means.

FIGS. 35 and 36 also show pitch bar 147. The pitch bar 147 is a non-moving, but radially adjustable (with respect to drum 1), T-shaped element. The horizontal portion 147a of the pitch bar is slidably mounted in a perforation 148 in block 149. Block 149, itself, is fixed to side plate 64 of head 3 by screws 150 and 151. The portion 147a of the pitch bar has a plurality of transverse perforations (not shown) therethrough which can be individually aligned with a vertical perforation (not shown) in block 149. A pin 152 passes through the aligned holes in block 149 and pitch bar portion 147a to hold the pitch bar in any desired radial position. The pitch bar is steadied by a spring 153 mounted on portion 147a and abutting block 149 and vertical portion 147b of the pitch bar.

The purpose of the pitch bar is to contact the tube 5 between heads enabling the pitch length between heads to be adjusted. Each head of the machine is provided with a pitch bar.

The clamp and shear assembly 27 comprises a first bracket 154 affixed to the exterior of side plate 64 by cap screws 155 and 156, or the like. The bracket 154 supports the pad 27d of urethane or similar resilient material. The shear blade 27a is pivoted to bracket 154 as at 157. The clamping block 27b is affixed to the shear blade. An extension 158 is also mounted to the shear blade. The rod end 91 of actuating rod 89 is pivotally affixed to the extension 158, as at 159. Bracket 154 also supports anvil 27c with which shear blade 27a cooperates.

It will be evident from FIG. 35, that as the actuating rod 89 is caused to shift to the right by stationary cam surface 55 (see FIG. 20) the shear blade 27a will pivot about pivot point 157 in a counter-clockwise direction. This will cause the shear blade 27a to shear against anvil 27c and the clamping block 27b to abut the resilient pad 27d. As a result of this, string located in the nip between anvil 27c and shear blade 27a will be cut by the blade and the left hand end of the string (as viewed in FIG. 36) will be clamped between the clamping block 27b and resilient pad 27d. The parts are so arranged that the string is clamped before it is cut.

Figure 41:
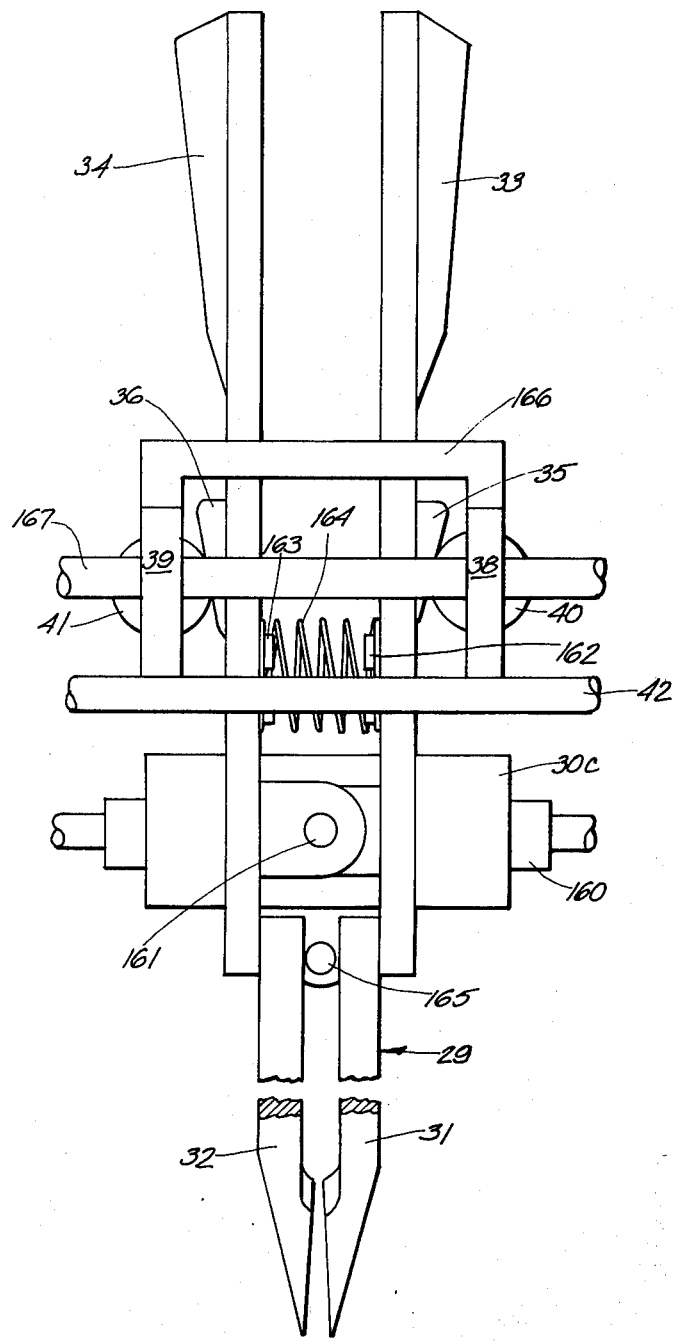
FIG. 41 is a fragmentary auxiliary view of the spreader-pliers.

FIGS. 38 through 41 illustrate the spreader-pliers 29. A shaft 160 is rotatively mounted between side plates 64 and 65. The pliers actuator 30 comprises a pair of upstanding members 30a and 30b non-rotatively affixed to shaft 160. The members 30a and 30b support a platform 30c to which the pliers jaws 31 and 32 are pivotally affixed so as to be shiftable toward and away from each other. In FIGS. 38 and 41, the jaws 31 and 32 are shown pivoted to platform 30c by pivot pin 161.

As is most clearly illustrated in FIGS. 40 and 41, the jaws 31 and 32 are provided on their facing surfaces with cap screws 162 and 163. These cap screws serve as supports for the end of a spring 164 which urges the jaws 31 and 32 to their closed position. The platform 30c also carries an upstanding pin 165 which maintains the jaws 31 and 32 of the spreader-pliers properly centered relative to the needle mechanism when the jaws are closed.

The rearward end of spreader-pliers jaw 31 supports the large cam element 33 and the small cam element 35 while the rearward end of jaw 32 supports large cam element 34 and small cam element 36. Cam elements 33 and 35 are adapted to cooperate with cam wheel 40, while cam elements 34 and 36 are adapted to cooperate with cam wheel 41.

Cam wheels 40 and 41 are mounted on blocks 38 and 39, respectively. The blocks 38 and 39 are joined together by a plate 166, so that the cam wheels will act in unison. Blocks 38 and 39 are pivotally mounted upon a shaft 167 non-rotatively supported between side plates 64 and 65. When the cam wheels 40 and 41 are in their normal positions, the blocks 38 and 39 lie in abutment with a stop bar 42, as shown in FIGS. 38 and 41. The stop bar 42 comprises a shaft extending between side plates 64 and 65.

A third block 168 is non-rotatively mounted on shaft 167 between blocks 38 and 39. Block 168 is illustrated in FIGS. 38 through 40, but has been eliminated from FIG. 41 for purposes of clarity. The block 168 rests on top of stop bar 42. Spring means 169 (not shown in FIG. 41) is mounted on shaft 167 and has one of its ends affixed to block 38 and the other of its ends affixed to block 168. In similar fashion, a second spring means 170 is mounted on shaft 167 with one of its ends affixed to block 39 and the other of its ends affixed to block 168. The purpose of springs 169 and 170 is to bias blocks 38 and 39 against stop bar 42, thus biasing cam wheels 40 and 41 to their normal positions.

The spreader-pliers actuator 27 has on its portion 30a a rearward extension 171, the free end of which is pivotally connected to the rod end 91 of actuating rod 89, as at 172 (see FIG. 38). Thus, it will be evident that if actuating rod 89 is shifted to the right (as viewed in FIG. 38) by stationary cam 51 (see FIG. 20), the actuator 30 and the spreader-pliers 29 carried thereby will rotate in a clockwise direction. As the pliers rotate, they will be opened slightly by small cam elements 35 and 36, whereupon they will close. Thereafter, they will be opened again by large cam elements 33 and 34 permitting them to pass the needle 22. As soon as the large cam elements 33 and 34 pass beyond cam wheels 40 and 41, the spreader-pliers jaws 31 and 32 will snap together, engaging the cut ends of string 7 held in the string tensioners as described with respect to FIGS. 10 and 11.

As the actuating rod 89 is caused to shift to the left in FIG. 38, the actuator 30 and spreader-pliers 29 will rotate in a counter-clockwise direction. The large cams 33 and 34 will abut cam wheels 40 and 41 shifting them in a clockwise direction out of the way and against the urging of springs 169 and 170. As soon as the small cams 35 and 36 have cleared cam wheels 40 and 41, the cam wheels will return to their normal position shown in the figures under the influence of springs 169 and 170. This was described above in conjunction with FIGS. 13 and 15. Finally, the actuating rod 89 will again shift to the right to the extent that small cam elements 35 and 36 will be engaged by cam wheels 40 and 41 to enable the spreader-pliers jaws 31 and 32 to release the string 7 and the product to the discharge transfer wheel 4, as described with respect to FIG. 17.

Modifications may be made in the invention without departing from the spirit of it. For purposes of an exemplary showing, the invention has been described in an embodiment wherein the drum 1 is provided with 45 operating heads. It will be understood that more or fewer heads could be used by making appropriate design changes in the machine elements depending also, of course, on the size of the product being handled.

It would also be within the scope of the invention to provide a single head, the operating instrumentalities of which are appropriately actuated. For example, such a single head could be maintained stationary and a rotating cylindrical member equivalent to member 48 (FIG. 19) bearing cam surfaces 50 through 55 could be provided. In such an instance, the product components would be hand-fed to or indexed through the head.

While the process and apparatus of the present invention have been described in their application for the production of sack-like products to be ultimately formed into tampons, it will be understood by one skilled in the art that the process and apparatus may be applied to any appropriate product requiring loop knot string tying. This is true whether a single head, hand fed, is used or whether the automatic machine as described, with multiple heads, is used. For example, the machine may be used to tie strings to clothing tags, identification tags or the like either singly, or provided to the machine in the form of a continuous web. Where the product being loop knotted does not require selected ones of the steps described above, the operating instrumentalities performing those steps may be eliminated. For example, if sealing is not required the heating coil 21 may be eliminated. Where pleating is not required, pleating jaw assemblies 15 and 18 may be eliminated.

The needle 22 may form a hole in the product, as described above. Alternatively, the needle may pass through a preformed hole in the product. When the product is of such nature that the simple loop knot is to be formed about the product rather than through a perforation therein, the clamping means may be modified to hold the product in such position that the needle passes thereabove. This will cause the simple loop knot 43 to be formed about the product rather than through it. This is illustrated in FIG. 42. FIG. 42 is essentially the same as FIG. 11. The operating instrumentalities are the same and like parts have been given like index numerals. The only difference between FIGS. 42 and 11 lies in the fact that the parts have been adjusted in FIG. 42 to cause the needle 22 to pass above, rather than through, the tube or product 5. As a consequence, a simple loop knot will be formed about but not through the tube or product 5.

The embodiments of the invention in which an exclusive property or privilege is claimed are defined as follows:

1. Apparatus for forming a simple loop knot of segment of flexible strand-like material about a portion at least of a product, said apparatus comprising a head, means on said head for clamping and holding said product in a position to receive said loop knot, means on said head for forming said strand segment into a U-shaped loop behind said product, said U-shaped loop having a pair of legs joined by a base portion, means on said head for frictionally engaging the free ends of said loop legs, means on said head for engaging the base portion of said strand loop and carrying said base portion of said loop forwardly of said product and about said portion at least thereof and means on said head for removing said free ends of said loop legs from said frictional engagement means and drawing said free ends through said base portion of said strand loop to form said simple loop knot.

2. The apparatus claimed in claim 1 wherein said clamping and holding means comprise a pair of clamping jaw assemblies in parallel spaced relationship, each clamping jaw assembly comprising first and second clamping jaws, means for shifting said first and second clamping jaws between an open position and a closed position wherein said product is held therebetween, said portion at least of said product about which said loop knot is formed being located between said pair of clamping jaw assemblies.

3. The apparatus claimed in claim 1 including means for shifting said means for engaging said base portion of said strand loop between a fully retracted position behind said product, through a strand loop base portion engaging position behind said product and to fully extended position forwardly of said product along a path of travel adjacent said product so as to carry said base portion of said strand loop forwardly of said product whereby said loop knot is formed about said product.

4. The apparatus claimed in claim 1 including means to shift said means for engaging said base portion of said strand loop between a fully retracted position behind said product, through a strand loop base portion engaging position behind said product and to fully extended position forwardly of said product along a path of travel through a preformed hole in said product whereby said means for engaging said strand loop base portion pulls said base portion of said loop through said hole and said loop knot is formed through and about a portion of said product.

5. The apparatus claimed in claim 1 including means to shift said means for engaging said base portion of said strand loop between a fully retracted position behind said product, through a strand loop base portion engaging position behind said product and to a fully extended position forwardly of said product along a path of travel through said product whereby said means for engaging said base portion of said loop pierces a hole in said product and pulls said loop base portion therethrough, said loop knot being formed through and about a portion of said product.

6. The apparatus claimed in claim 1 wherein said means for removing said free ends of said strand loop legs from said frictional engagement means and drawing said free ends through said base portion of said strand loop comprises a pliers-like element having a pair of jaws, means for shifting said pliers-like element along a path of travel through said base portion of said strand loop between a fully retracted position and a fully extended position wherein said jaws engage said free ends of said loop legs, and means for opening said jaws during the shifting of said pliers-like element from said fully retracted position to said fully extended position and means for closing said jaws on said free ends of said strand loop legs and maintaining said jaws closed during the shifting thereof from said fully extended to said fully retracted position.

7. The apparatus claimed in claim 1 including means to pleat said product prior to engagement thereof by said clamping and holding means.

8. Apparatus for continuously forming a simple loop knot of a segment of flexible strand-like material about a portion at least of each product in a continuous web of product material, said apparatus comprising in combination a single continuous source of said web of product material, a single continuous source of said flexible strand-like material and a cylindrical drum rotatable about a vertical axis, a plurality of identical heads mounted on said drum at the periphery thereof and evenly spaced thereabout, means to rotate said drum so that each of said heads continuously follows a circular path of travel through pick up points for said strand and said web of product material, through an active portion of the drum cycle wherein each head operates upon a segment of said product web to form said loop knot about a portion at least of a product thereof and through a product discharge point, each of said heads having a plurality of operating instrumentalities comprising means for clamping and holding said product web segment in a position to receive said loop knot, means for metering said strand segment from said continuous strand and forming said strand segment into a U-shaped loop behind said web segment, said U-shaped loop having a pair of legs joined by a base portion, means to shear said metered strand segment from said strand and to clamp the free end of said strand to advance said strand about said drum until the metered strand segment of the next adjacent upstream head is sheared, tensioner means for frictionally engaging the free ends of said strand loop legs, means for engaging the base portion of said strand segment loop and carrying said base portion of said loop forwardly of said web segment and about said portion at least thereof, pliers means for removing said free ends of said strand loop legs from said tensioner means and drawing said free ends through said base portion of said strand loop to form said simple loop knot, and means to actuate said operator instrumentalities in the proper sequence.

9. The apparatus claimed in claim 8 wherein said clamping means comprises an upstream clamping jaw assembly and a downstream clamping jaw assembly in parallel spaced relationship within said head, each clamping jaw assembly comprising first and second clamping jaws, said first and second clamping jaws being shiftable by said actuating means between an open position and a closed position wherein said product web segment is held therebetween, said portion at least of said product in said web about which said loop knot is formed being located between said pair of clamping jaw assemblies.

10. The apparatus claimed in claim 8 wherein said string metering and loop forming means is shiftable by said actuating means between a fully retracted position adjacent said tensioner means and an extended strand loop forming position behind said product web segment.

11. The apparatus claimed in claim 8 wherein said means for engaging said base portion of said strand loop is shiftable by said actuating means between a fully retracted position behind said product web segment, through a strand loop base portion engaging position behind said product web segment and to a fully extended position forwardly of said product web segment along a path of travel adjacent said product web segment so as to carry said base portion of said strand loop forwardly of said product web segment whereby said loop knot is formed about a product of said web segment.

12. The apparatus claimed in claim 8 wherein said means for engaging said base portion of said strand loop is shiftable by said actuating means between a fully retracted position behind said product web segment, through a strand loop base portion engaging position behind said product web segment and to a fully extended position forwardly of said product web segment along a path of travel through a preformed hole in a product of said web whereby said means for engaging said base portion of said strand loop pulls said base portion through said hole and said loop knot is formed through and about a portion of said product of said web segment.

13. The apparatus claimed in claim 8 wherein said means for engaging said base portion of said strand loop is shiftable by said actuating means between a fully retracted position behind said product web segment, through a strand loop base portion engaging position behind said product web segment and to a fully extended position forwardly of said product web segment along a path of travel through a product of said web segment whereby said means for engaging said base portion of said strand loop pierces a hole in said product of said web segment and pulls said strand loop base portion therethrough, said loop knot being formed through and about a portion of said product of said web segment.

14. The apparatus claimed in claim 8 wherein said means for removing said free ends of said strand loop legs from said tensioner means and drawing said free ends through said base portion of said strand loop comprises a pliers-like element having a pair of jaws, said pliers-like element being shiftable along a path of travel through said base portion of said strand loop by said actuating means between a fully retracted position and a fully extended position wherein said jaws engage said free ends of said strand loop legs, and means for opening said jaws during the shifting of said pliers-like element from said fully retracted position to said fully extended position and means for closing said jaws on said free ends of said strand loop legs and maintaining said jaws closed during the shifting thereof from said fully extended to said fully retracted position.

15. The apparatus claimed in claim 8 including means to pleat said product web segment prior to engagement thereof by said clamping and holding means.

16. The apparatus claimed in claim 8 wherein said means to actuate said instrumentalities comprises a stationary cylindrical member located within and concentric with said rotatable drum, said cylindrical member having a plurality of cam surfaces about its periphery, each of said instrumentalities of each head being supported by its respective head and being operatively connected to one end of an actuating rod, the other end of said actuating rod being operatively connected to a cam follower adapted to contact the appropriate one of said cam surfaces and means to maintain said cam follower in contact with its respective one of said cam surfaces.

17. The apparatus claimed in claim 8 including means to sever said web segment after formation of said loop knot whereby the product of said web segment loop knotted at each head is detached from the product of said web segment loop knotted by the next adjacent downstream head.

18. The apparatus claimed in claim 8 including product pitch adjustment means affixed to each of said heads, said pitch adjustment means each comprising an elongated pitch bar having a free end adapted to contact that portion of said web material between said head to which said pitch bar is affixed and the next adjacent head, means to adjust the position of said free end of said pitch bar radially of said drum whereby to compensate for change in product length in said web of product material.

19. The apparatus claimed in claim 8 wherein said web of product material comprises a tube of flexible fluid-permeable material having measured increments of absorbent material therein spaced from each other by a distance equal to one product length, peripheral glue stripes being printed on said tube equidistant between said increments of absorbent material, means to pleat said web segment prior to engagement thereof by said clamping and holding means, said clamping and holding means comprising an upstream clamping jaw assembly and a downstream clamping jaw assembly in parallel spaced relationship within said head, each clamping jaw assembly comprising first and second clamping jaws, said first and second clamping jaws being shiftable by said actuating means between an open position and a closed position wherein said product web segment is held therebetween, said portion at least of said product in said web about which said loop knot is formed being located between said pair of clamping jaw assemblies, said downstream clamping jaw assembly of each head engaging said web at the position of a glue stripe thereon, means to heat said downstream clamping jaw assembly to seal said web segment at the position of a glue stripe thereon, means to sever said web segment after formation of said loop knot whereby the product of said web segment loop knotted at each head is detached from the product of said web segment loop knotted at the next adjacent downstream head to form individual products each comprising a sack of said flexible fluid-permeable material having therein a measured increment of absorbent material, said sack being pleated at both ends, one end being sealed and the other end being closed by said loop knotted strand segment.

20. The apparatus claimed in claim 9 wherein said first clamping jaws of said upstream and downstream clamping jaw assemblies are shiftable longitudinally by said actuating means between said open and closed positions, said second clamping jaws of said upstream and downstream clamping jaw assemblies being rotatable by said actuating means between said open and closed positions, means independently spring loading said first clamping jaws whereby to assure that they will seat with equal force against their respective second clamping jaws with said web therebetween when said clamping jaws are in said closed position.

21. The apparatus claimed in claim 10 wherein said string metering and loop forming means comprises a bifurcated element, the free ends of said bifurcations being notched to engage said strand segment and to display said base portion as said strand segment loop between said free ends of said bifurcations for engagement by said means for engaging said base portion of said strand segment loop.

22. The apparatus claimed in claim 11 wherein said means for engaging said base portion of said strand loop comprises an elongated element having a free end and a strand engaging notch adjacent said free end.

23. The apparatus claimed in claim 12 wherein said means for engaging said base portion of said strand loop comprises an elongated element having a free end and a strand engaging notch adjacent said free end.

24. The apparatus claimed in claim 13 wherein said means for engaging said base portion of said strand loop comprises an elongated needle having a free pointed end and a strand engaging notch adjacent said free end.

25. The apparatus claimed in claim 14 wherein said fully retracted position of said pliers-like element lies on one side of said web segment and said fully extended position lies on the other side of said web segment, said path of travel of said pliers-like element lying forwardly of said web segment and said means for opening said jaws during the shifting of said pliers-like element from said fully retracted to said fully extended positions comprising cam means so configured as to cause said jaws to pass to either side of said means for engaging said base portion of said strand loop.

26. The apparatus claimed in claim 15 wherein said pleating means comprises a pair of pleating jaw assemblies, each pleating jaw assembly comprising upper and lower pleating jaws shiftable by said actuating means between open and closed positions, said upper and lower pleating jaws of each assembly having pleating teeth which lie in interdigitated relationship when said jaws are in said closed position.

27. The apparatus claimed in claim 17 wherein said severing means comprises a blade supported on said strand metering and loop forming means.

28. The apparatus claimed in claim 19 wherein said means for engaging said base portion of said strand loop comprises an elongated needle having a free pointed end and a strand engaging notch adjacent said free end, said needle being shiftable by said actuating means between a fully retracted position behind said product web segment, through a strand loop base portion engaging position behind said product web segment and to a fully extended position forwardly of said product web segment along a path of travel through a product of said web segment whereby said needle pierces a hole in said product of said web segment and pulls said base portion of said strand loop therethrough, said loop knot being formed through and about a portion of said product of said web segment.

29. The apparatus claimed in claim 19 wherein said means for removing said free ends of said strand loop legs from said tensioner means and drawing said free ends through said base portion of said strand loop comprises a pliers-like element having a pair of jaws, said pliers-like element being shiftable along a path of travel through said base portion of said strand loop by said actuating means between a fully retracted position and a fully extended position wherein said jaws engage said free ends of said strand loop legs and means for opening said jaws during the shifting of said pliers-like element from said fully retracted position to said fully extended position and means for closing said jaws on said free ends of said strand loop legs and maintaining said jaws closed during the shifting thereof from said fully extended to said fully retracted position, said pliers-like element being shiftable by said actuating means from said fully retracted position to a partially extended position after said product loop knotted by said head supporting said pliers has been severed from said web by the next adjacent upstream head whereby said pliers-like element displays said product by said loop knotted strand segment and means for slightly opening said jaws when said pliers-like element is in said partially extended position whereby to release said product to appropriate transfer means.

30. The apparatus claimed in claim 24 wherein said needle has a triangular cross section.

31. The apparatus claimed in claim 30 wherein said needle is configured as an arc of a circle, said path of travel being arcuate about the center of said circle.

32. A method of forming a simple loop knot of a segment of flexible strand-like material about a portion at least of a product comprising the steps of clamping and holding said product in a position to receive said loop knot, forming said strand segment into a U-shaped loop behind said product, said U-shaped loop having a pair of legs joined by a base portion, frictionally engaging and holding the free ends of said strand loop legs, engaging the base portion of said strand loop and carrying said base portion forwardly of said product and about said portion at least thereof, releasing said free ends of said strand loop legs and drawing said free ends through said base portion of said strand loop to form said loop knot.

33. The method claimed in claim 32 wherein said base portion of said strand loop is carried forwardly of said product along a path of travel adjacent said product whereby said loop knot is formed about said product.

34. The method claimed in claim 32 wherein said base portion of said strand loop is carried forwardly of said product along a path of travel through a preformed hole in said product whereby said loop knot is formed through and about a portion of said product.

35. The method claimed in claim 32 including the steps of piercing a hole through said product and carrying said base portion of said strand loop forwardly of said product along a path of travel through said hole whereby said loop knot is formed through and about a portion of said product.

36. The method claimed in claim 32 including the step of pleating said product prior to said clamping and holding thereof.

37. A method of continuously forming a simple loop knot of a segment of flexible strand-like material about a portion at least of each product in a continuous web of product material comprising the steps of providing a single continuous source of said web of product material, providing a single continuous source of said flexible strand-like material, providing a cylindrical drum rotatable about a vertical axis and having a plurality of identical heads mounted on said drum at the periphery thereof and evenly spaced thereabout, rotating said drum so that each of said heads continuously follows a circular path of travel through pick up points for said strand and said web of product material, through an active portion of the drum cycle wherein each head operates upon a segment of said product web to form said loop knot about a portion at least of a product thereof and through a product discharge point, at each of said heads clamping and holding a segment of said product web in a position to receive said loop knot, metering said strand segment from said continuous strand and forming said strand segment into a U-shaped loop behind said product, said U-shaped loop having a pair of legs joined by a base portion, shearing said metered strand segment from said strand and clamping the free end of said strand to advance said strand about said drum until the metered strand segment of the next adjacent upstream head is sheared, frictionally engaging the free ends of said strand loop legs, engaging the base portion of said strand segment loop and carrying said base portion of said loop forwardly of said product web segment and about said portion at least thereof, releasing said free ends of said strand loop legs and drawing them through said base portion of said strand loop to form said simple loop knot.

38. The method claimed in claim 37 including the step of pleating said web segment prior to said clamping and holding thereof.

39. The method claimed in claim 37 wherein said base portion of said strand loop is carried forwardly of said web segment along a path of travel adjacent said web segment whereby said loop knot is formed about a product in said web segment.

40. The method claimed in claim 37 wherein said base portion of said strand loop is carried forwardly of said web segment along a path of travel through a preformed hole in said web segment whereby said loop knot is formed through and about a portion of a product in said web segment.

41. The method claimed in claim 37 including the steps of piercing a hole through said web segment and carrying said base portion of said strand loop forwardly of said web segment along a path of travel through said hole whereby said loop knot is formed through and about a portion of a product in said web segment.

42. The method claimed in claim 37 including the step of severing said web segment after formation of said loop knot whereby a product of said web segment loop knotted at each head is detached from the product of said web segment loop knotted at the next adjacent downstream head.

43. The method claimed in claim 37 wherein said web of product material comprises a tube of flexible fluid-permeable material having measured increments of absorbent material therein spaced from each other by a distance equal to one product length and having peripheral glue stripes printed thereon equidistant between said increments of absorbent material, and including the steps of pleating said web segment prior to the clamping and holding thereof, applying heat to said web segment to seal said web segment at the position of said glue stripe thereon and severing said web segment after formation of said loop knot whereby a product of said web segment loop knotted at each head is detached from a product of said web segment loop knotted at the next adjacent downstream head to form individual products each comprising a sack of said flexible fluid-permeable material having therein a measured increment of absorbent material, said sack being pleated at both ends, one end being sealed and the other end being closed by said loop knotted strand segment.

44. The method claimed in claim 43 including the step of suspending and displaying said sack for pick-up by an appropriate transfer means.

\* \* \* \* \*

UNITED STATES PATENT AND TRADEMARK OFFICE
CERTIFICATE OF CORRECTION

PATENT NO. : 3,940,169
DATED : February 24, 1976
INVENTOR(S) : Ronald W. Kock

It is certified that error appears in the above-identified patent and that said Letters Patent are hereby corrected as shown below:

Column 5, line 24, "11b illustrated" should read --11b are illustrated--.

Column 10, line 3, "extend" should read --extent--.

Column 19, line 47, "knot of segment" should read --knot of a segment--.

Column 20, line 46, "said loop" should read --said strand loop--.

Column 21, line 25, "operator" should read --operating--.

Column 21, line 64, "web whereby" should read --web segment whereby--.

Column 23, line 45, "as" should read --of--.

Signed and Sealed this

Eleventh Day of January 1977

[SEAL]

Attest:

RUTH C. MASON
Attesting Officer

C. MARSHALL DANN
Commissioner of Patents and Trademarks